United States Patent
Marshall et al.

(10) Patent No.: US 11,498,018 B2
(45) Date of Patent: Nov. 15, 2022

(54) EXTRACTION AND PURIFICATION OF CANNABINOID COMPOUNDS

(71) Applicant: BELEAVE INC., Hamilton (CA)

(72) Inventors: John G. Marshall, Toronto (CA); Lesley G. Campbell, Toronto (CA)

(73) Assignee: Vasilios (Bill) Panagiotakopoulos, Toronto (CA)

( * ) Notice: Subject to any disclaimer, the term of this patent is extended or adjusted under 35 U.S.C. 154(b) by 0 days.

(21) Appl. No.: 16/201,547

(22) Filed: Nov. 27, 2018

(65) Prior Publication Data

US 2019/0160393 A1 May 30, 2019

Related U.S. Application Data

(60) Provisional application No. 62/591,053, filed on Nov. 27, 2017.

(51) Int. Cl.
*B01D 11/02* (2006.01)
*C07D 311/80* (2006.01)

(52) U.S. Cl.
CPC ...... *B01D 11/0288* (2013.01); *B01D 11/0219* (2013.01); *C07D 311/80* (2013.01)

(58) Field of Classification Search
None
See application file for complete search history.

(56) References Cited

U.S. PATENT DOCUMENTS

| 4,551,542 A | * | 11/1985 | Moore | C07D 311/68 549/401 |
| 2015/0045282 A1 | * | 2/2015 | Elsohly | A61P 27/06 514/1.3 |
| 2017/0226077 A1 | * | 8/2017 | Bach | C07D 311/80 |
| 2017/0266245 A1 | | 9/2017 | Scialdone | |
| 2018/0000879 A1 | * | 1/2018 | Nadal Roura | A61K 36/185 |

FOREIGN PATENT DOCUMENTS

| CA | 2499492 A1 | 1/2004 |
| WO | WO 2017/051398 A1 | 3/2017 |

* cited by examiner

*Primary Examiner* — Richard C Gurtowski
(74) *Attorney, Agent, or Firm* — Holbeche Law; Kevin Edward Holbeche

(57) ABSTRACT

Disclosed are effective methods for activating, washing, specifically extracting and purifying cannabinoids from *Cannabis* plant tissues using heat activation, washing impurities away with a polar solvent, optionally modified with an organic acid, base, surfactant or inorganic salt, extracting the activated non-polar cannabinoids with a potable selective solvent such as ethanol. The extracted active ingredients may be purified by chromatography and detected and quantified by mass spectrometry with external or isotopic or otherwise labelled standards.

17 Claims, 40 Drawing Sheets

EXTRACTION AND PURIFICATION OF CANNABINOID COMPOUNDS

FIELD OF THE INVENTION

The present invention relates to methods for the extraction of cannabinoid compounds from plant tissue.

BACKGROUND

It may be desirable to extract cannabinoid compounds from plant tissue, particularly the flower or leaves of hemp or marijuana plants such as *Cannabis sativa, C. indica* or *C. ruderalis*. The most common cannabinoids of interest are cannabidiol (CBD) and tetrahydrocannabinol (THC). THC and CBD are non-polar isoprenoid compounds that are frequently found modified with carboxylic acid groups that renders them both polar and inactive (THCA and CBDA). THCA and CBDA can be decarboxylated by heat, causing the compounds to be both activated and rendered non-polar (lipophilic). The activation, i.e. decarboxylation, of CBDA or THCA results in the active ingredients CBD or THC. However, the activation of THC and CBD limits the solubility of THC and CBD in water, while rendering them soluble in organic solvents.

It is well known that activated cannabinoids may be extracted from plant tissue using organic solvents such as chloroform, acetonitrile, butane, hexane, isopropanol, butanol, methanol and others. However, these non-potable solvents may be harmful themselves or be contaminated with trace amounts of harmful solvents.

It is also known to use supercritical carbon dioxide ($CO_2$) to extract cannabinoids, and while supercritical $CO_2$ extraction leaves no residual solvents that might be toxic or harmful, it is a difficult and slow process. A $CO_2$ extraction can take 8 to 24 hours and require precise parameters to obtain acceptable selectivity. It also needs extremely high pressures to be useful, leading to high equipment costs.

There remains a need in the art for effective and economic methods of extracting cannabinoids from plant tissue, without the use of toxic or non-potable solvents.

SUMMARY OF THE INVENTION

In one aspect, the invention comprises a method of extracting a cannabinoid from a plant tissue, comprising the steps of:

(a) heating the plant tissue to convert carboxylated cannabinoid to a non-polar active form;

(b) washing the plant tissue with a polar solvent; and (c) extracting the non-polar cannabinoid with a selective solvent.

Optionally, the plant tissue may be dried and/or ground before the heat activation step. Preferably, the polar solvent comprises water, a water/alcohol mixture, an organic acid, or a salt solution, and may optionally include a surfactant. The selective solvent is one which selectively extracts cannabinoid compounds. In some embodiments, the heated, activated plant tissue may be extracted with the selective solvent to produce an intermediate resin before washing with a polar solvent in step (b). Preferably, the selective solvent comprises ethanol or ethyl acetate.

Conversion of non-active, carboxylated forms of cannabinoids into their non-polar active ingredients allows for the subsequent, preferential removal of components which are soluble in a polar solvent. The cannabinoids may then be extracted using a selective solvent, such as ethanol, which is preferred due to its potability. Non-polar activated cannabinoids such as THC and CBD are not soluble in polar solvents, therefore polar contaminants may be washed away using the polar solvent. The polar solvent may be modified with salts, buffers or inorganic or organic acids or bases. The non-polar cannabinoids may then be extracted in a potable selective solvent, such as ethanol, that contains no harmful residues.

Optionally, the extracted cannabinoids may be purified by chromatography and/or quantified by spectroscopic methods.

In some embodiments, *cannabis* plant tissue is heated using an oven or a water bath to cause the conversion of the native acid forms of the cannabinoids, such as tetrahydrocannabinolic acid (THCA) and cannabidiolic acid (CBDA), to the non-polar active ingredients THC and CBD. In some embodiments, the plant tissue is heated at a temperature between about 100° to about 140° C., for between about 30 minutes to about 2 hours, preferably at about 120° C. for about 1 hour.

In some embodiments, the washing step uses a polar solvent comprising water, a water/alcohol mixture, water modified by salt, buffers, inorganic or organic acids or bases, potable organic solvents, and/or combinations thereof. In some embodiments, the tissue or intermediate resin is washed in a polar solvent comprising a potable surfactant or emulsifying agent, such as deoxycholate or n-octylglucoside or other amphipathic detergents. Preferably, the washing step is done at a refrigerated temperature, such as below about 5° C., more preferably below about 0° C., but obviously above the freezing temperature of the polar solvent.

In some embodiments, the heated and washed *cannabis* tissue is subsequently extracted with a potable organic solvent, such as >40% ethanol and preferably 80% ethanol (v:v). Preferably, the extraction step occurs at a refrigerated temperature, such as between about −80° C. to about 5° C., and more preferably between about −20° C. and about 0° C. In view of the teachings and disclosures herein, persons having ordinary skill in the art shall readily appreciate that the refrigerated extraction temperature will be higher than the potable organic solvent's freezing temperature. And, in further view of the teachings and disclosures herein persons having ordinary skill in the art shall readily appreciate that the refrigerated extraction temperature will be lower than the potable organic solvent's flashpoint temperature—i.e., the temperature at which the potable organic solvent would give off sufficient vapor to ignite in air and/or would form an ignitable mixture in air near the surface of the potable organic solvent.

In an embodiment, the active cannabinoids extracted from washed tissue by the selective solvent may be subsequently purified or separated from other extracted components by chromatography, the separation may be performed by liquid chromatography (LC), optionally DEAE, CMC, QA, PS, normal phase, or reversed phase chromatography. The chromatography may be isocratic, step gradient or a linear gradient.

In yet another embodiment, the purity of the purified active ingredient may be quantified by liquid chromatography such as high-performance liquid chromatography (HPLC). In an embodiment, the HPLC is nanoflow liquid chromatography. In another embodiment, the HPLC can be reverse phase HPLC, ion exchange HPLC or normal phase HPLC. The chromatography mobile phase can for example be isopropyl alcohol (IPA), methanol, ethanol, propanol, or acetonitrile. The stationary phase can for example be silica based or polymer based, for example silica particles modified with octadecyl carbon chain (C18).

In an embodiment, the step of detecting one or more ionizable products using mass spectrometry (MS) comprises ionizing the one or more ionizable products, optionally by electrospray ionization (ESI) or Atmospheric Pressure Chemical Ionization (APCI) to produce one or more product ions with a selected signal-to-noise ratio, and subjecting the one or more product ions to MS, optionally tandem MS (MS/MS). In another embodiment, the ionizing is positive ionization (e.g. using an acidic buffer in the mobile phase). In another embodiment, the ionizing is negative ionization (e.g using a basic buffer in the mobile phase). In an embodiment, the step of ionizing the one or more ionizable products comprises Matrix-assisted laser desorption/ionization (MALDI).

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

DETAILED DESCRIPTION

Figure 1:
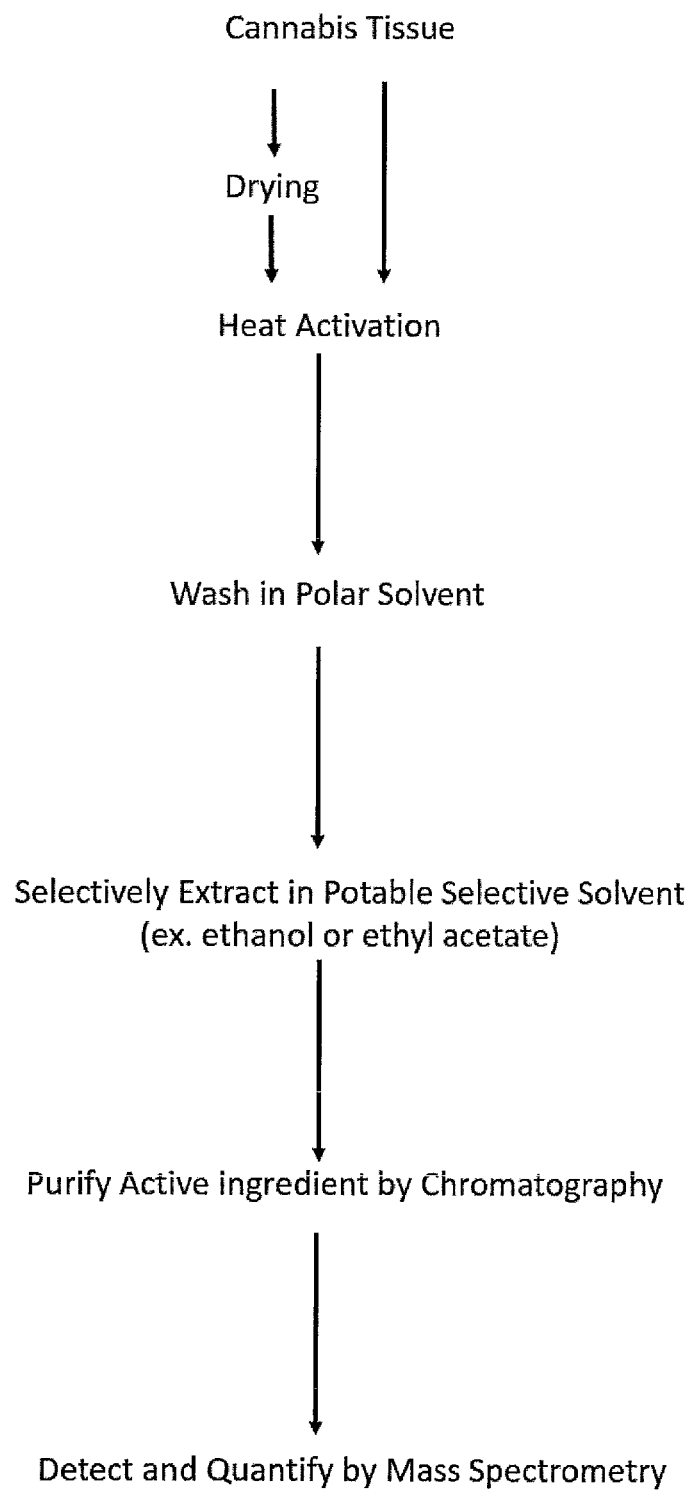
FIG. 1 is an illustration of a scheme to activate, wash, selectively extract, purify, identify and quantify the cannabinoid compounds.

The present invention comprises methods of selectively extracting and purifying cannabinoids from plant tissue, such as cannabinoid plant tissue.

Cannabinoids are compounds which act on or modulate cannabinoid receptors in cells, which can alter neurotransmitter release in the brain. Cannabinoids were originally found in *Cannabis saliva* L., the origin of marijuana and hashish. Marijuana or its components have been reported in the scientific literature to alleviate the symptoms of a broad range of conditions including multiple sclerosis and forms of muscular spasm, including uterine and bowel cramps; movement disorders; pain, including migraine headache; glaucoma, asthma, inflammation, insomnia, and high blood pressure. There may also be utility for cannabinoids as an oxytoxic, anxiolytic, anti-convulsive, anti-depressant and/or anti-psychotic agent, anti-cancer agent, or an appetite stimulant.

Many chemically related compounds, collectively classified as cannabinoids, have been isolated from *Cannabis* plants. The cannabinoids usually divided in the groups of classical cannabinoids, non-classical cannabinoids, aminoalkylindole derivatives and eicosanoids. Classical cannabinoids such as THC or CBD are isolated from *Cannabis sativa* L., or they can comprise synthetic analogs of these compounds. Non-classical cannabinoids may comprise bi- or tricyclic analogs of tetrahydrocannabinol (THC), while aminoalkylindoles form a group which differs structurally substantially from classical and non-classical cannabinoids.

In various embodiments, cannabinoids can include, but are not limited to, cannabinoid compounds that may naturally occur in different combinations and relative quantities in the plant tissues of various species, subspecies, hybrids, strains, chemovars, and other genetic variants of the genus *Cannabis*, including material that may variously be classified as "marijuana" and "hemp" in accordance with various legal or technical definitions and standards.

An exemplary cannabinoid comprises THC, having the formula (I):

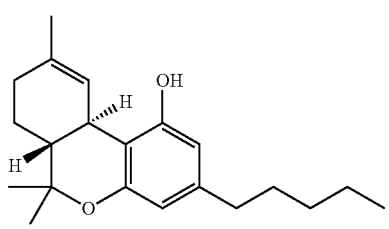

(I)

which includes delta-9-tetrahydrocannabinol (D9THC), acknowledged to be the main psychoactive compound in marijuana. Another exemplary cannabinoid is cannabidiol (CBD) IUPAC: 2-[(1R,6R)-6-isopropenyl-3-methylcyclohex-2-en-1-yl]-5-pentylbenzene-1,3-diol, having the formula (II):

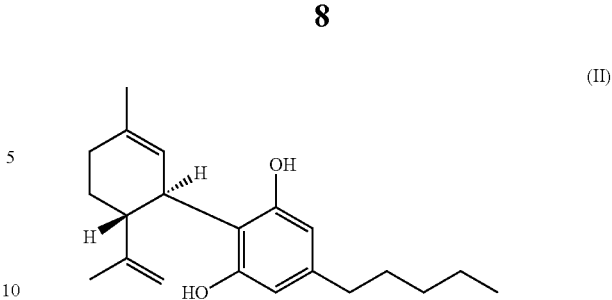

(II)

Although CBD is not known to have the psychotropic effects of THC, it is still considered to have a wide scope of potential therapeutic applications. CBD may be derived from industrial hemp which has negligible amounts of THC, and may be legally grown and consumed in Canada and the United States.

Cannabinoid compounds may also include various other cannibinoids such as tetrahydrocannabinolic acid (THCA), delta-8-tetrahydrocannabinol (D8THC), cannabidiolic acid (CBDA), cannabinol (CBN), cannabinolic acid (CBNA), tetrahydrocannabinovarin (THCV), tetrahydrocannabinovarinic acid (THCVA), cannabidivarin (CBDV), cannabidivarin acid (CBDVA), cannabigerol (CBG), cannabigerolic acid (CBGA), cannabichromene (CBC), cannabichromenic acid (CBCA), cannabinodiol (CBND), and cannabinodiolic acid (CBNDA).

The term "selective" as used herein in reference to a solvent, a solid phase or chromatography system of a solvent or solid phase, is one that selectively extracts or purifies a target substance or compound, such as a cannabinoid, with greater specificity relative to another different substance or compound. In some embodiments, the selective system purifies the target substance or compound by at least 2 fold, 3 fold, or 5 fold.

FIG. 1 is an illustration of a general scheme to activate, wash, selectively extract, purify, identify and quantify cannabinoid compounds from *cannabis* plant tissue. Accordingly, in one aspect, the invention may comprise a method of selectively extracting and purifying a cannabinoid from plant tissue comprising the steps of:
  a. preparing plant tissue in fresh or dried form;
  b. heating the tissue to decarboxylate cannabinoid compounds;
  c. optionally, extracting the tissue with a selective solvent to produce an intermediate resin;
  d. washing the tissue or resin with an polar solvent to selectively remove compounds soluble in the polar solvent while leaving decarboxylated cannabinoid compounds;
  e. selectively extracting the cannabinoid from the plant tissue using a selective solvent to produce a cannabinoid extract.

Preferably, the cannabinoids from the extract can be purified by precipitation and/or partition chromatography drying. Finally, the cannabinoids can be detected by liquid chromatography electrospray or atmospheric pressure ionization and tandem mass spectrometry (MS/MS).

The methods disclosed herein may be performed on finely divided plant tissue, such as fresh or dried tissue which has been cut, chopped, ground, mashed or otherwise processed to reduce particle size. The method may also be performed in solution in the absence of a solid phase, wherein the target substance is not in the solid phase but in a colloidal suspension or fine powder in water or otherwise suspended or emulsified in a liquid phase.

Preferably, the polar solvent comprises purified water, or water mixed with alcohol such as ethanol, preferably less than about 40% ethanol (v:v), or acetic acid, preferably less than about 5% acetic acid (v:v). It is preferred that all components are potable. As used herein, a potable component is one that is classified as "Generally Regarded as Safe" or "GRAS" by the United States FDA.

Polar solvents have large dipole moments ("partial charges"); that is they contain bonds between atoms with very different electronegativities, such as oxygen and hydrogen. Non polar solvents contain bonds between atoms with similar electronegativities, such as carbon and hydrogen. Bonds between atoms with similar electronegativities will lack partial charges. In one embodiment, the polar solvent is one with a dielectric constant greater than about 5.0 at 20° C., preferably greater than about 20, and more preferably greater than about 50.

In some embodiments, the washing polar solvent comprises a non-ionic, non-polymeric detergent or a bile acid detergent, such as sodium deoxycholate. In an embodiment, the wash solvent contains a potable buffer such as phosphate or carbonate buffer, such as $Na_2CO_3$ or $NaHCO_3$, an organic acid, such as acetic acid or formic acid, ammonia, ammonium hydroxide, methylamine trimethylamine or the like.

It is preferred that the polar solvent wash take place at a reduced temperature, preferably below about 5° C., and more preferably below about 00° C., but obviously above the freezing temperature of the solvent.

In some embodiments, multiple washes with different polar solvents is preferred. For example, a first wash in 0.5% acetic acid (v:v) may be repeated up to three times, followed by a second wash in 40% ethanol (v:v), repeated up to three times. Without restriction to a theory, it is believed that an initial wash in a weak organic acid may protonate water-soluble impurities, facilitating their dissolution in the aqueous phase. The subsequent washes in ethanol/water selectively removes additional polar impurities.

The selective solvent is one which selectively extracts the activated (decarboxylated) cannabinoid, and may be polar or non-polar. Preferably, the extract solvent comprises ethanol, or ethanol mixed in water, preferably greater than about 40% ethanol (v:v), more preferably 80% ethanol. Potable ethanol is intended for human consumption and contains no unacceptable residues of harmful solvents.

In some embodiments, the cannabinoid is selectively extracted with about 80% ethanol at a refrigerated temperature, preferably between about −80° C. and about 5° C., and more preferably between about −20° C. and 0° C. In view of the teachings and disclosures herein, it should be appreciated that the refrigerated extraction temperature will be higher than the 80% ethanol's freezing temperature and lower than its flashpoint temperature.

Extraction may be followed by precipitation or drying to recover the desired cannabinoid compounds.

The extracted compounds may be purified by liquid partition chromatography as monitored by electrospray ionization or atmospheric pressure chemical ionization and tandem mass spectrometry (LC-ESI-MS/MS) is more sensitive and definitive than colorimetric, fluorescent, flame ionization, or electron capture detection and permits standards labelled with isotopes or isobaric tags. Since mass spectrometers can separate and analyze many analytes simultaneously using the methods described herein, it can allow identification and quantification of many different cannabinoids at the same time to levels far below that which is possible by direct mass spectrometric analysis.

While the present application has been described with reference to what are presently considered to be preferred examples, it is to be understood that the application is not limited to the disclosed examples. To the contrary, the application is intended to cover various modifications and equivalent arrangements included within the spirit and scope of the appended claims.

Examples

The following examples are intended to illustrate specific embodiments of the claimed invention, and not be limiting in any way.

Mass Recovery 0.1 g Hemp was heated to 120° C. for 1 hour prior to extraction with various solvents: ethanol, methanol, acetonitrile, isopropyl alcohol, ethyl acetate and acetone. 3 sequential extracts were pooled. Samples were dried to determine the mass extracted and redissolved for mass spectrometry analysis to measure CBD content. Total CBD was set to 1.7082 mg/100 mg. The results are shown in Table 1 below

TABLE I

Mass yields after extraction with different solvents (n = 3).

| Extraction solvent | mass extracted (mg) from 100 mg hemp | CBD (mg) from 100 mg hemp | % mass recovery from total in tissue | % CBD of mass extracted |
|---|---|---|---|---|
| EtOH | 7.004692478 | 0.7931933 | 46.43282818 | 11.32 |
| MeOH | 6.772186616 | 0.8139417 | 47.64742232 | 12.02 |
| AcN | 3.839389904 | 0.9036164 | 52.8968976 | 23.54 |
| IPA | 5.506566586 | 0.7875847 | 46.10450387 | 14.30 |
| Ethyl Acetate | 5.569882112 | 0.9563186 | 55.9820377 | 17.17 |
| Acetone | 4.758931245 | 0.7973442 | 46.6758185 | 16.75 |

The first column—(((Tube+dried extract)−tube)*100 mg hemp)/actual weight of hemp (mg).

The second column—STD curve equation used to find concentration of CBD. Then, CBD (mg)=(Mw×V(L)× M)×1000. Standardize to 100.00 mg hemp: ((CBD (mg)*100 mg)/actual hemp (mg)

Mass recovery ($3^{rd}$ column)=(CBD(mg)/CBD Total (mg))*100%

$4^{th}$ column=(CBD (mg)/mass extract (mg))*100%

Figure 11:
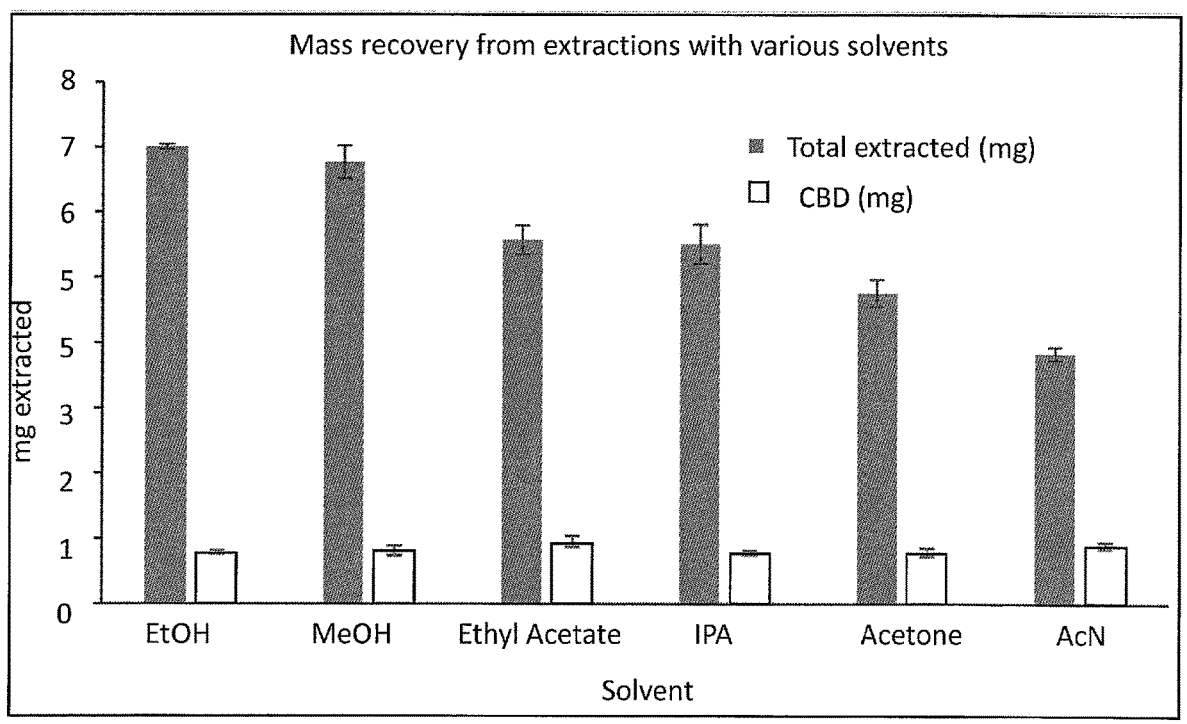
FIG. 11. Mass recovery after extraction with different solvents (n=3). A, 0.1 g Hemp was heated to 120° C. for 1 hour prior to extraction with various solvents. Mass yields after extraction with different solvents (n=3). A, 0.1 g Hemp was heated to 120° C. for 1 hour prior to extraction with various solvents (3 sequential extracts were pooled). Samples were dried to determine the mass extracted and re-dissolved for mass spectrometry analysis to measure CBD content.
Figure 12A:
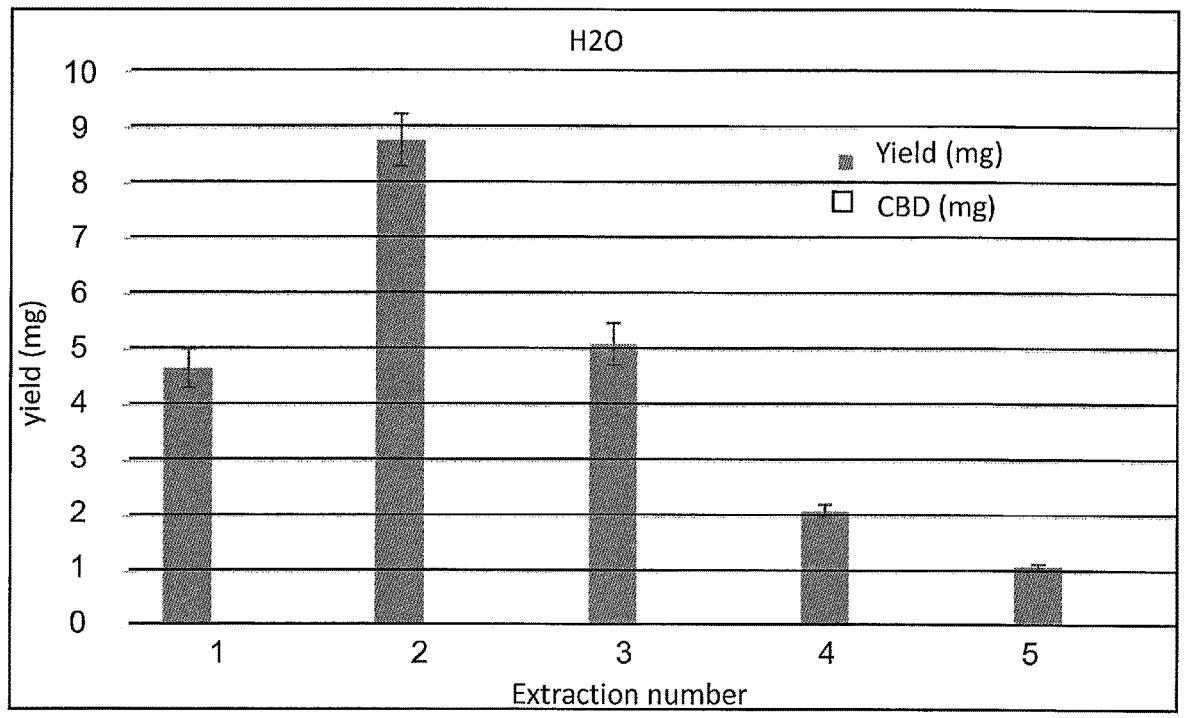
FIG. 12A. CBD yields from 5 sequential extractions for 0.1 g hemp heated to 120° C. for 1 hour and extracted in 5× H2O.
Figure 12B:
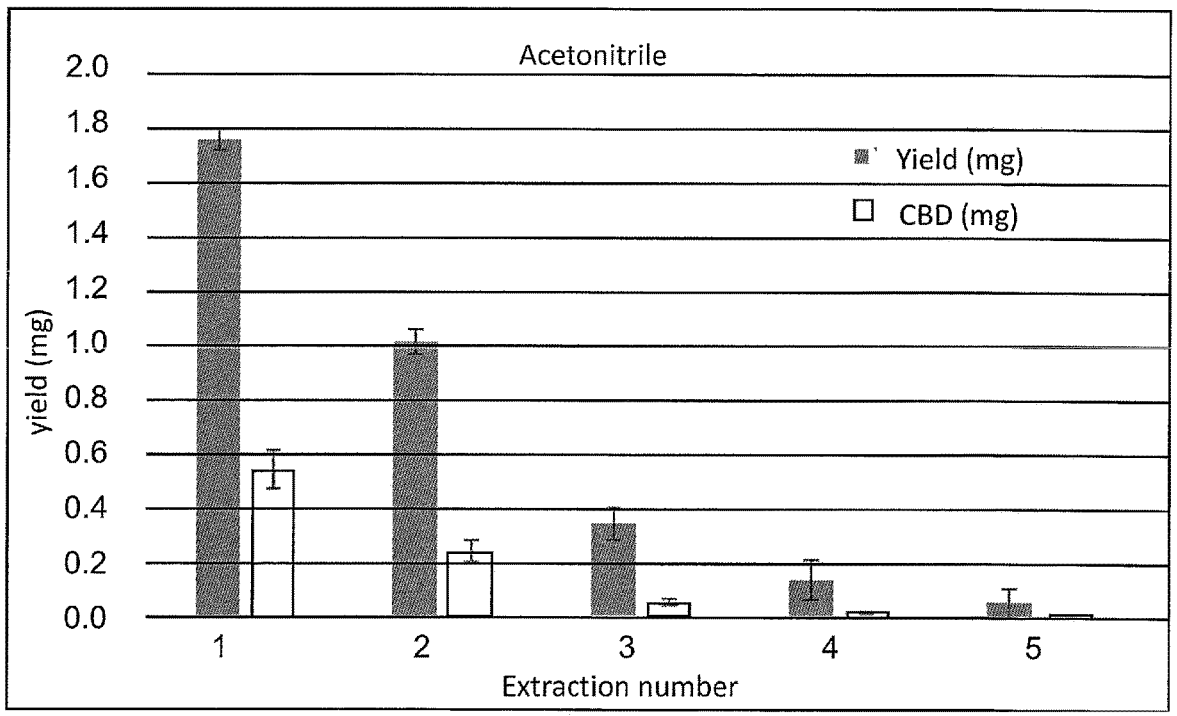
FIG. 12B. CBD yields from 5 sequential extractions for 0.1 g hemp heated to 120° C. for 1 hour and extracted in 5× Acetonitrile without pre-washing with H2O.
Figure 12C:
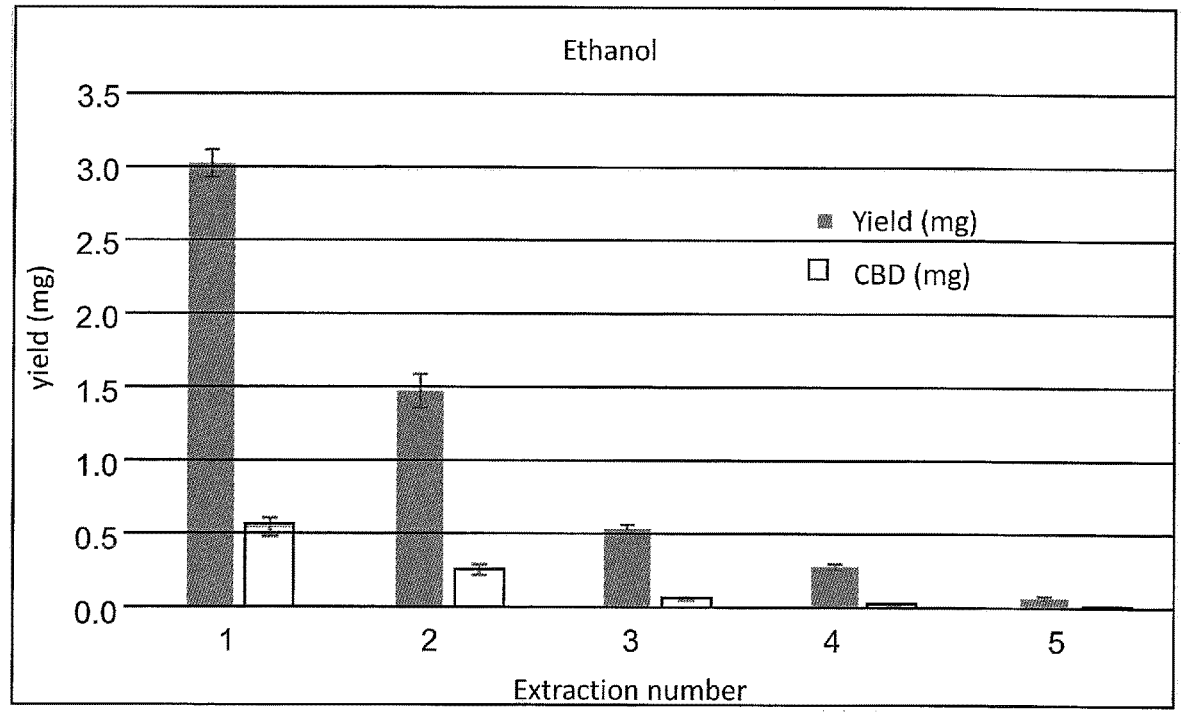
FIG. 12C. CBD yields from 5 sequential extractions for 0.1 g hemp heated to 120° C. for 1 hour and extracted in 5× Ethanol without pre-washing with H2O.
Figure 12D:
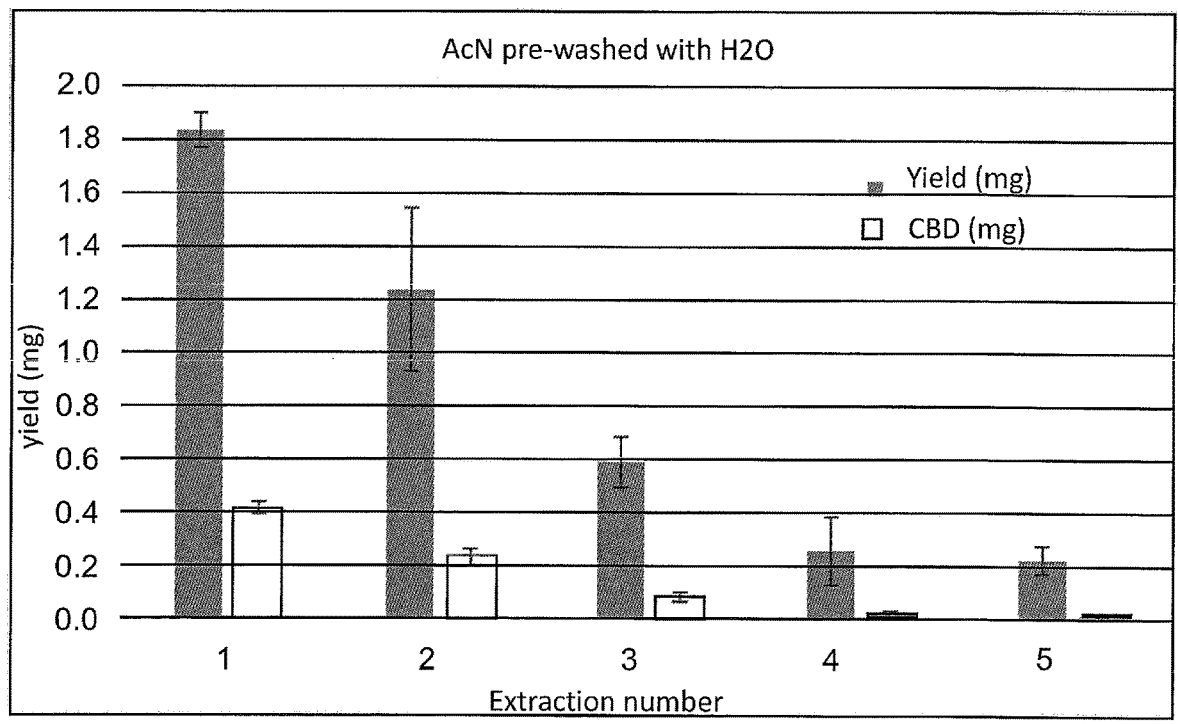
FIG. 12D. CBD yields from 5 sequential extractions for 0.1 g hemp heated to 120° C. for 1 hour and extracted in 5× Acetonitrile pre-washed with 5× H2O (n=3).
Figure 12E:
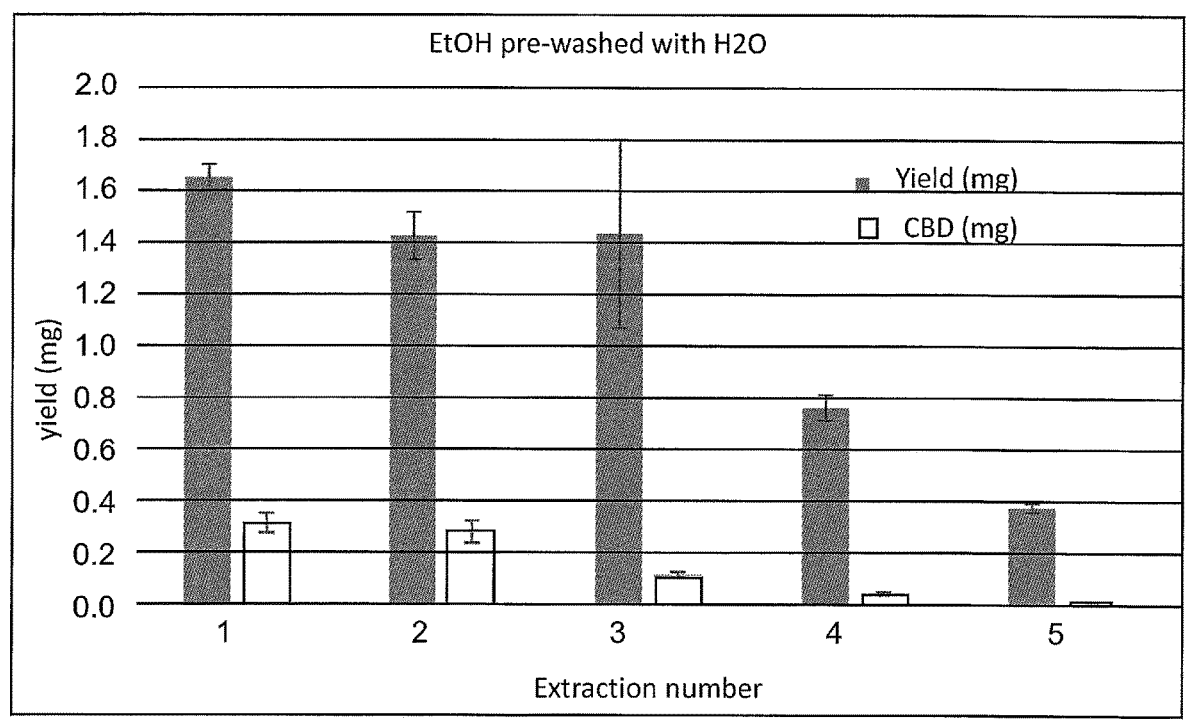
FIG. 12E. yields from 5 sequential extractions for 0.1 g hemp heated to 120° C. for 1 hour and extracted in 5× Ethanol pre-washed with 5× H2O (n=3).
Figure 13A:
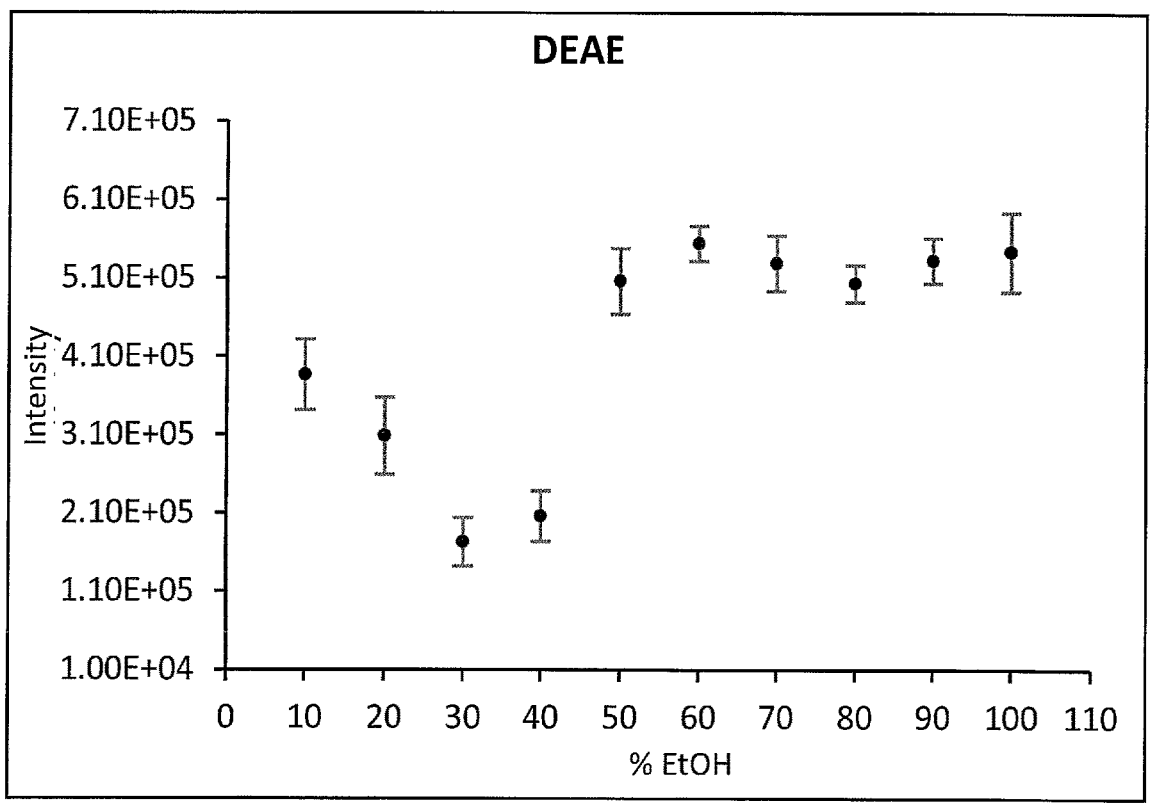
FIG. 13A. Optimizing binding conditions for CBD using ion exchange chromatography (n=3). 0.1 g of hemp was heated to 120° C. and extracted 3× in 100% ethanol. Extracts of 0.5 g total hemp per replicate were pooled and diluted with H2O to the appropriate ethanol concentrations. Samples were loaded at 100% ethanol and decreasing to 10% ethanol onto the DEAE resin. The Flow Throughs (FT) were collected and analyzed by LC-ESI-MS.
Figure 13B:
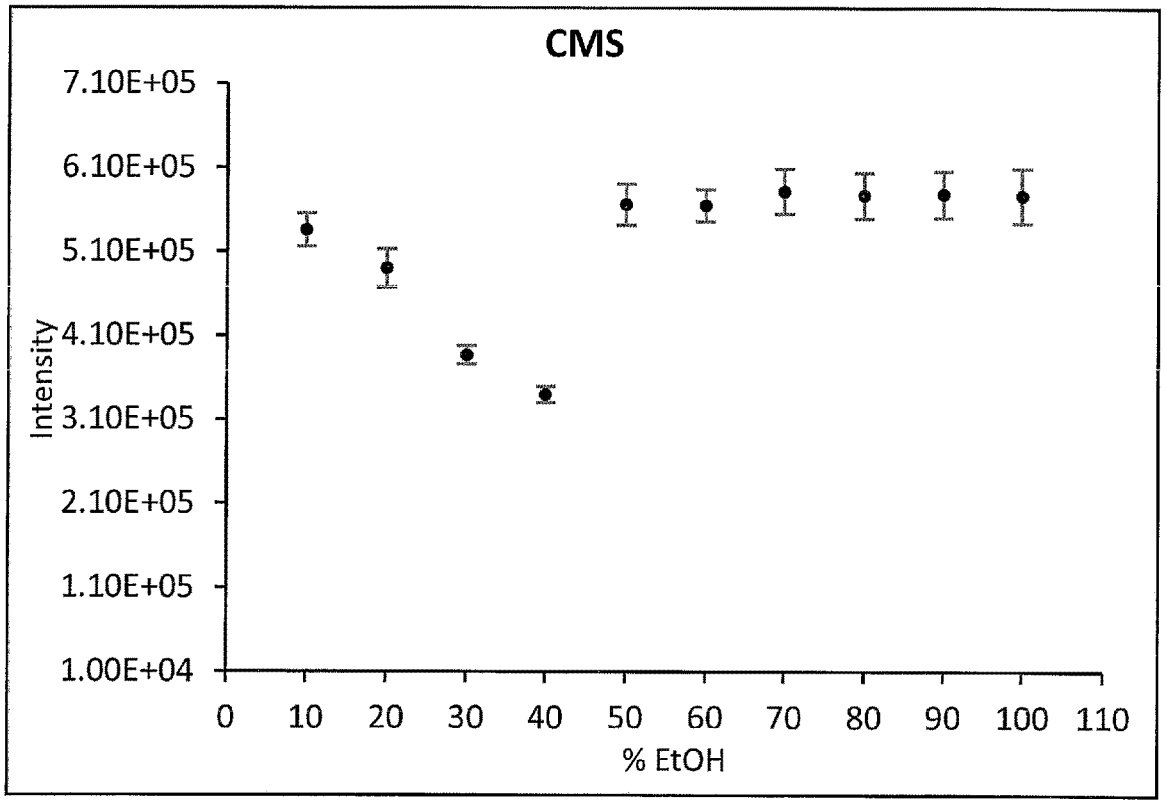
FIG. 13B. Optimizing binding conditions for CBD using ion exchange chromatography (n=3). 0.1 g of hemp was heated to 120° C. and extracted 3× in 100% ethanol. Extracts of 0.5 g total hemp per replicate were pooled and diluted with H2O to the appropriate ethanol concentrations. Samples were loaded at 100% ethanol and decreasing to 10% ethanol onto the CMS resin. The Flow Throughs (FT) were collected and analyzed by LC-ESI-MS.
Figure 13C:
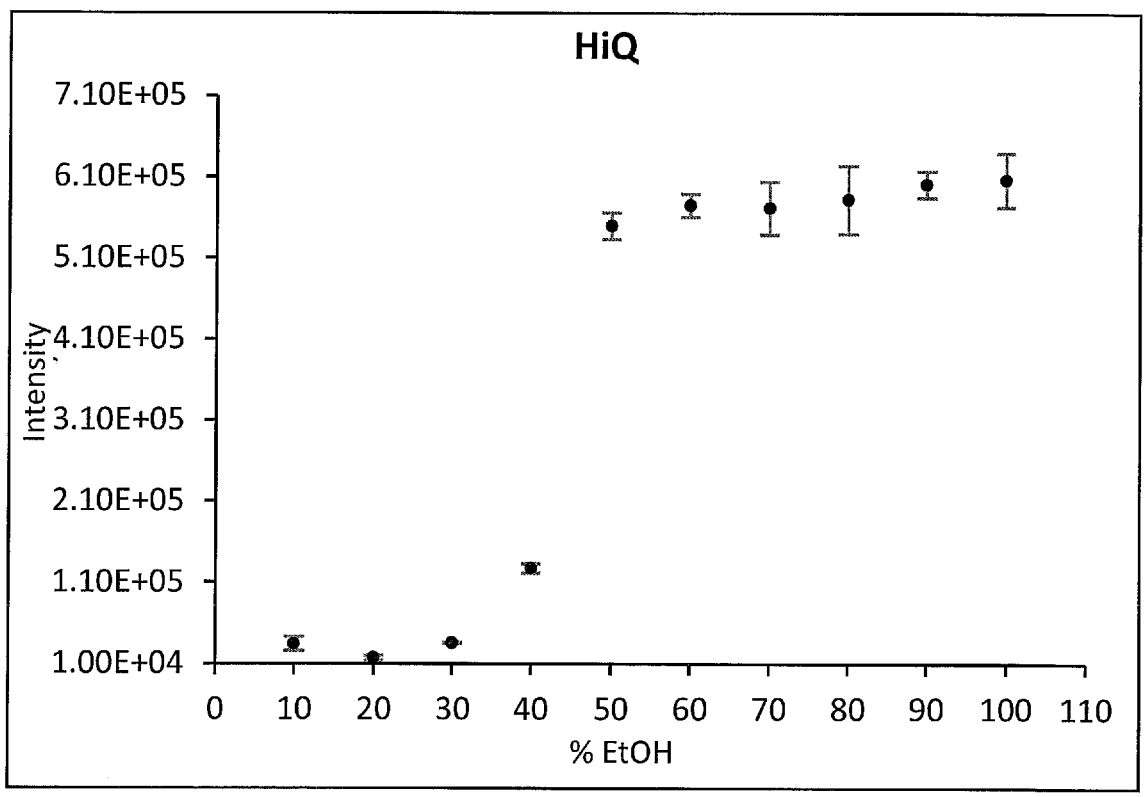
FIG. 13C. Optimizing binding conditions for CBD using ion exchange chromatography (n=3). 0.1 g of hemp was heated to 120° C. and extracted 3× in 100% ethanol. Extracts of 0.5 g total hemp per replicate were pooled and diluted with H2O to the appropriate ethanol concentrations. Samples were loaded at 100% ethanol and decreasing to 10% ethanol onto the HiQ resin. The Flow Throughs (FT) were collected and analyzed by LC-ESI-MS.
Figure 13D:
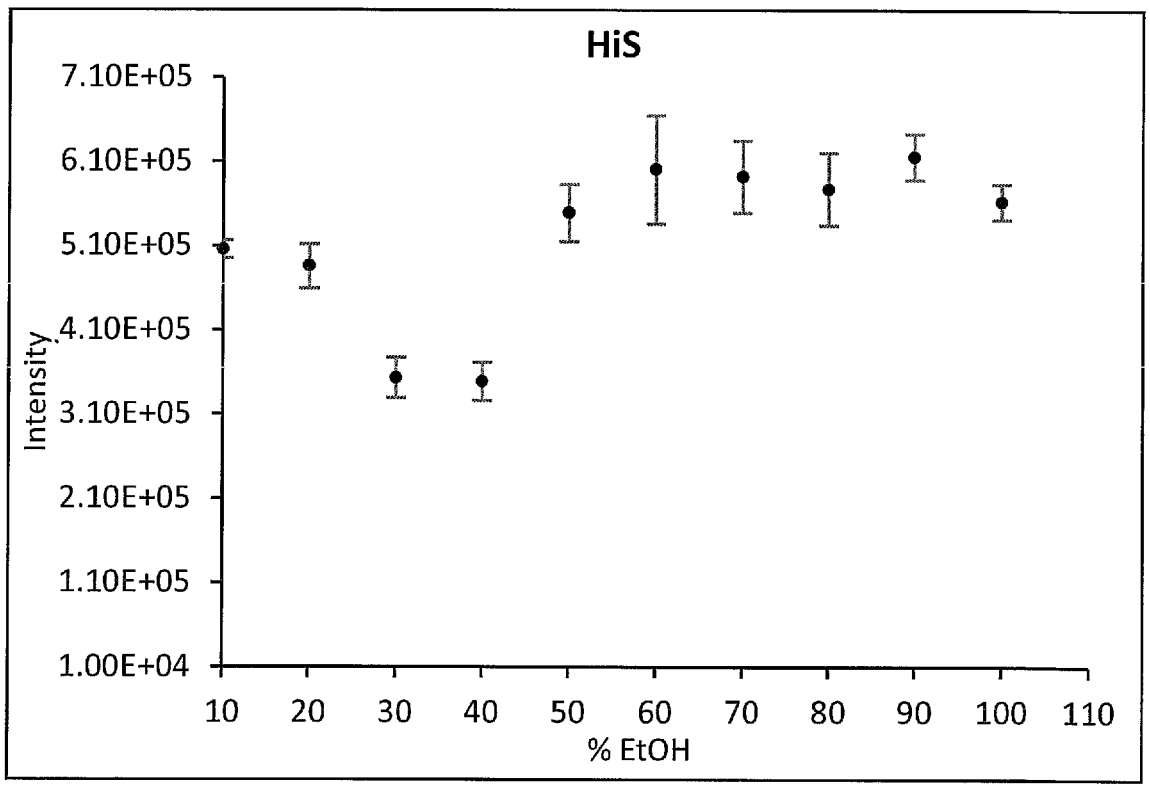
FIG. 13D. Optimizing binding conditions for CBD using ion exchange chromatography (n=3). 0.1 g of hemp was heated to 120° C. and extracted 3× in 100% ethanol. Extracts of 0.5 g total hemp per replicate were pooled and diluted with H2O to the appropriate ethanol concentrations. Samples were loaded at 100% ethanol and decreasing to 10% ethanol onto the HiS resin. The Flow Throughs (FT) were collected and analyzed by LC-ESI-MS.

The results are shown graphically in FIG. 11 and appear to indicate that the solvents are substantially similar in their ability to extract CBD.

Effect of Drying and Pre-washing 0.1 g hemp was heated to 120° C. for 1 hour and extracted in 3× 100% ethanol extraction with no pre-wash and without drying the extract (results in Table IIA); or in 80% ethanol extraction pre-washed with 3× water, 3× 40% ethanol and extracted once in 500 ul 80% ethanol (results in Table IIB). Samples were detected on a LC-ESI-MS using a 300 Angstrom 5 micron C18 porous resin.

TABLE IIA

Effect of drying on the re-solubilization of CBD and THC from cannabis tissue (n = 3).

|  | mass extracted (mg) from 100 mg tissue | CBD (mg)/100 mg tissue Extracted with 3x 100% Ethanol without pre-washing, without drying extract | CBD (mg)/100 mg tissue Extracted with 3x 100% Ethanol without pre-washing, extracts were dried to determine yield | % recovery from total in tissue | % CBD of mass extracted |
|---|---|---|---|---|---|
| rep1 | 6.858287815 | 1.058157929 | 1.122850101 | 65.7306445 | 16.3721636 |
| rep2 | 6.960101951 | 1.113238091 | 1.176511817 | 68.87195354 | 16.90365781 |
| rep3 | 7.001634043 | 1.106011877 | 1.187489191 | 69.51455927 | 16.96017221 |
| AVG | 6.940007936 | 1.092469299 | 1.162283703 | 68.03905244 | 16.74533121 |

TABLE IIB

Tissue extracted with 80% Ethanol was pre-washed with 3x water and 3x 40% ethanol and extracted 1x with 80% ethanol

|  | mass extracted (mg) from 100 mg tissue | CBD (mg)/100 mg tissue Extracted with 80% Ethanol with pre-washing in water and 40% ethanol, without drying extract | CBD (mg)/100 mg tissue Extracted with 80% Ethanol with pre-washing in water and 40% Ethanol, extracts were dried to determine yield | % recovery from total in tissue | % CBD of mass extracted |
|---|---|---|---|---|---|
| rep1 | 1.415841584 | 0.537632812 | 0.531468885 | 31.11171503 | 37.53731288 |
| rep2 | 1.411530815 | 0.59309931 | 0.521653691 | 30.53714231 | 36.95659249 |
| rep3 | 1.580516899 | 0.591777471 | 0.460355469 | 26.94879899 | 29.12689318 |
| AVG | 1.469296433 | 0.574169864 | 0.504492682 | 29.53255211 | 34.54026618 |

Multiple Extracts

CBD yields from 5 sequential extractions with and without pre-washing with water (n=3). 0.1 g hemp was heated to 120° C. for 1 hour and extracted in:

A, 5× H2O without pre-washing;
B, 5× Acetonitrile without pre-washing;
C, 5× Ethanol without pre-washing;
D, 5× Acetonitrile pre-washed with H2O;
E, 5× Ethanol pre-washed with H2O.

The mass yields and yield CBD of five fractions combined are shown in Table IIIA. The mass yields and yield CBD of the first three fractions combined are shown in Table IIIB. Samples were detected on a LC-ESI-MS using a 300 Angstrom 5 micron C18 porous resin. Mass is defined as the dry tissue product extracted.

TABLE III

The effect of multiple extracts of the yield and purity of CBD and THC from Cannabis tissue.

A.

| 5 sequential extracts combined | Dried hemp (mg) | Mass extract (mg) | CBD (mg) | % recovery from total in tissue | % recovery from total in tissue | % of mass extracted | % of extractable |
|---|---|---|---|---|---|---|---|
| H2O | 100 | 21.72245 | 0.00668 | 21.7224505 | 0.391161409 | 0.030761044 |  |
| AcN | 100 | 18.81004 | 0.851712338 | 18.81004126 | 49.85848141 | 4.527966344 |  |
| EtOH | 100 | 11.06295 | 0.88375334 | 11.06295159 | 51.73413315 | 7.988404947 |  |
| AcN pre-washed w 5x H2O | 100 | 6.30919 | 0.758266369 | 6.309190786 | 44.38823766 | 12.01844095 | 89.028459 |
| EtOH pre-washed w 5x H2O | 100 | 4.33586 | 0.762428385 | 4.335861815 | 44.63187836 | 17.58424086 | 86.271627 |

B.

| First 3 sequential extracts combined | Dried hemp (mg) | Mass extract (mg) | CBD (mg) | % recovery from total in tissue | % recovery from total in tissue | % of mass extracted | % of extractable |
|---|---|---|---|---|---|---|---|
| H2O | 100 | 18.50383 | 0.00592 | 18.50383271 | 0.346333151 | 0.031973212 |  |
| MN | 100 | 15.95629 | 0.830843944 | 15.95629159 | 48.63686421 | 5.206999 |  |
| EtOH | 100 | 8.31385 | 0.854943702 | 8.313853682 | 50.04764262 | 10.28336239 |  |
| AcN pre-washed w 5x H2O | 100 | 4.96295 | 0.72285888 | 4.962954964 | 42.31551479 | 14.56509045 | 87.0029667 |
| EtOH pre-washed w 5x H2O | 100 | 3.85851 | 0.703263897 | 3.858510015 | 41.16844198 | 18.22630743 | 82.2585038 |

The results are shown graphically in FIGS. 12A-12E.

Effect of Pre-Wash with Salt, Acid or Base 0.1 g of hemp was heated to 120° C. and pre-washed 3× with PBS, PBS+600 mM NaCl, 0.5% acetic acid (Hac), 0.5% ammonia or $H_2O$, followed by 3 washes of 40% Ethanol. CBD was then extracted with 3× 500 ul of 80% Ethanol and the three fractions were pooled. The samples pre-washed in $H_2O$ were extracted 1× with 1 ml of Ethanol.

TABLE IV-A

Effect of pre-washing with salt, acid or base on the extraction efficiency of CBD from hemp (n = 3).

| Pre-wash | Mass extract (mg) from 0.100 g hemp | CBD (mg) from 0.100 g hemp | % recovery from total in tissue | % of mass extracted |
|---|---|---|---|---|
| PBS | 3.9401649 | 0.76486 | 44.774197 | 19.40 |
| PBS + 600 mM NaCl | 10.7597825 | 0.67671 | 39.6142859 | 6.92 |
| 0.5% HAc | 3.52848406 | 0.81832 | 47.9036073 | 23.34 |
| 0.5% Ammonia | 4.15815607 | 0.76476 | 44.7686614 | 19.51 |
| H2O | 2.14577484 | 0.65554 | 38.3749606 | 30.54 |

In a separate experiment, samples were pre-washed in 3× water followed by 3 washes in 10%, 20%, 30% or 40% ethanol and extracted in 3×500 ul 80% ethanol. Fractions were pooled.

TABLE IV-B

| Pre-wash | Mass extract (mg) from 0.100 g hemp | CBD (mg) from 0.100 g hemp | % recovery from total in tissue | % of mass extracted |
|---|---|---|---|---|
| 10% EtOH | 3.51704 | 0.55792 | 32.6601693 | 15.86335 |
| 20% EtOH | 4.10537 | 0.5485614 | 32.1122937 | 13.36206 |
| 30% EtOH | 4.10044 | 0.5997451 | 35.1085456 | 14.62637 |
| 40% EtOH | 4.23101 | 0.5910847 | 34.6015711 | 13.97028 |

Figure 2A:
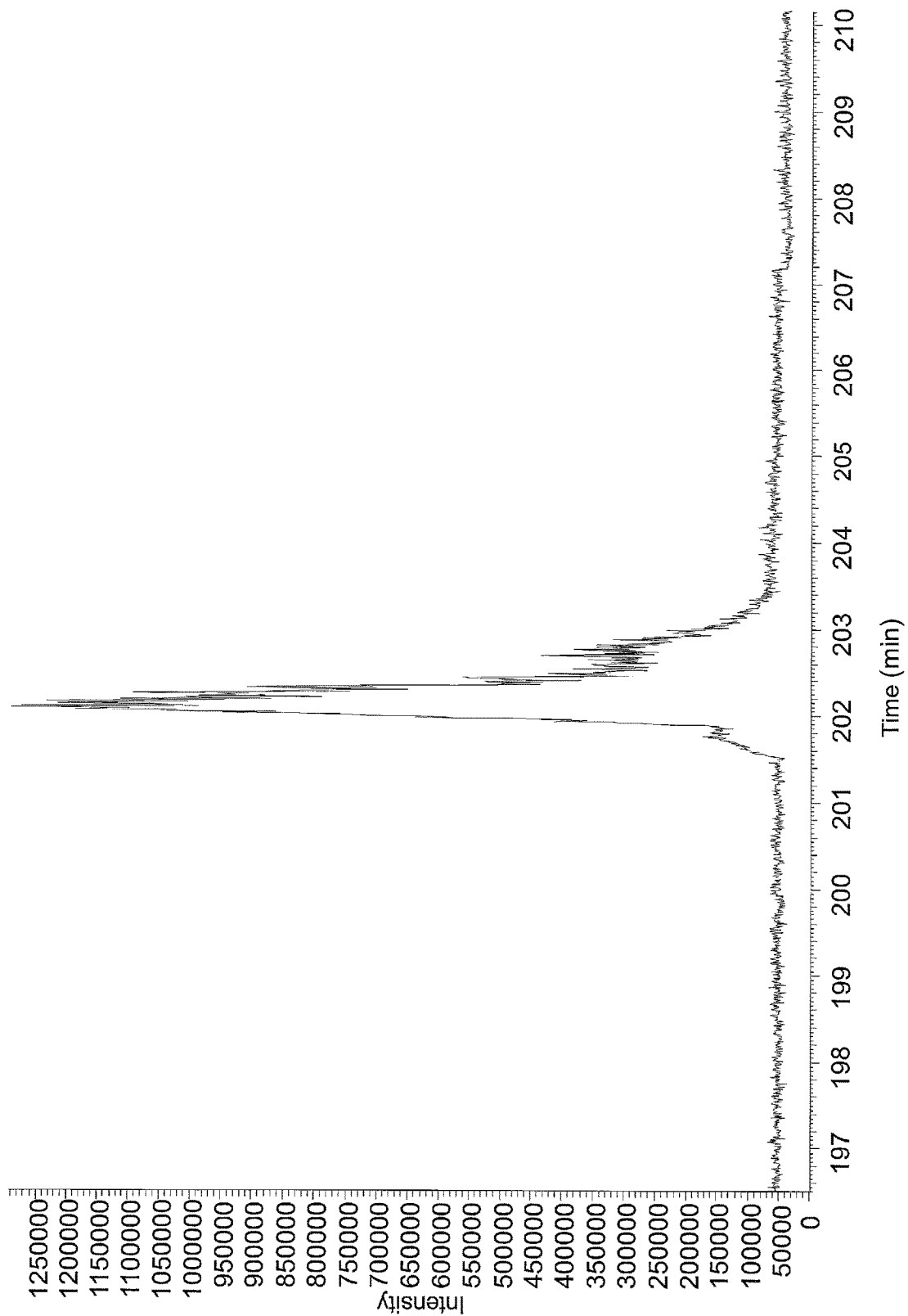
FIG. 2A. The separation and detection of CBD, and CBDa by isocratic HPLC in 70% AcN 0.1% formic acid of 100% Ethanol extract prior by 300 Angstrom 5 micron C18 porous resin to LC-ESI-MS (n=1). Note the porous resin does not resolve CBD from THC.
Figure 2B:
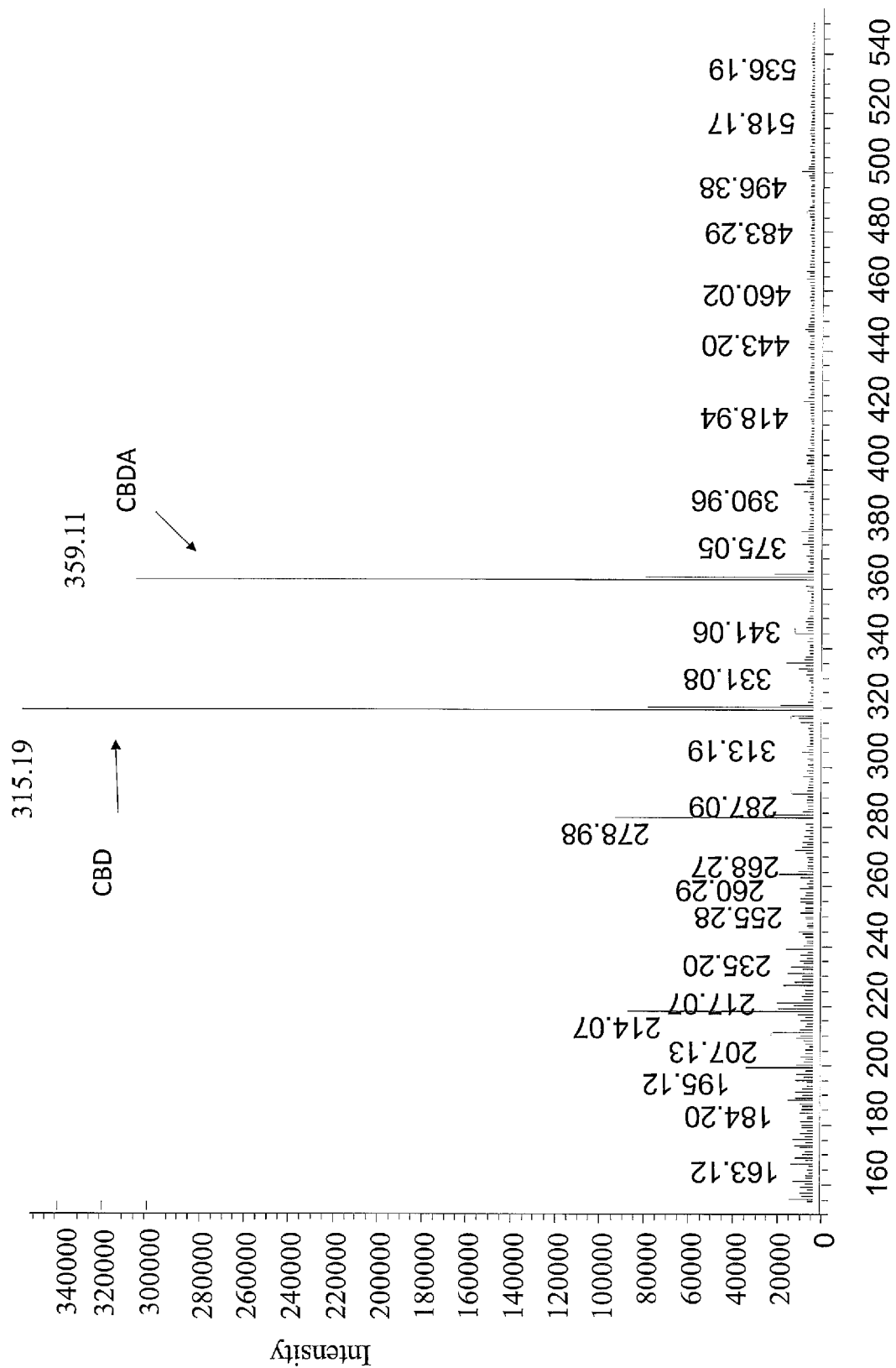
FIG. 2B. The separation and detection of THC and THCa by isocratic HPLC in 70% AcN 0.1% formic acid of 100% Ethanol extract prior by 300 Angstrom 5 micron C18 porous resin to LC-ESI-MS (n=1). Note the porous resin does not resolve CBD from THC.

FIGS. 2A and 2B shows the separation and detection of CBD, CBDa (FIG. 2A) THC and THCa (FIG. 2B) by isocratic HPLC in 70% AcN 0.1% formic acid, of a 100% Ethanol extract by 300 Angstrom 5 micron C18 porous resin to LC-ESI-MS (n=1). Note the porous resin does not resolve CBD from THC.

Figure 3:
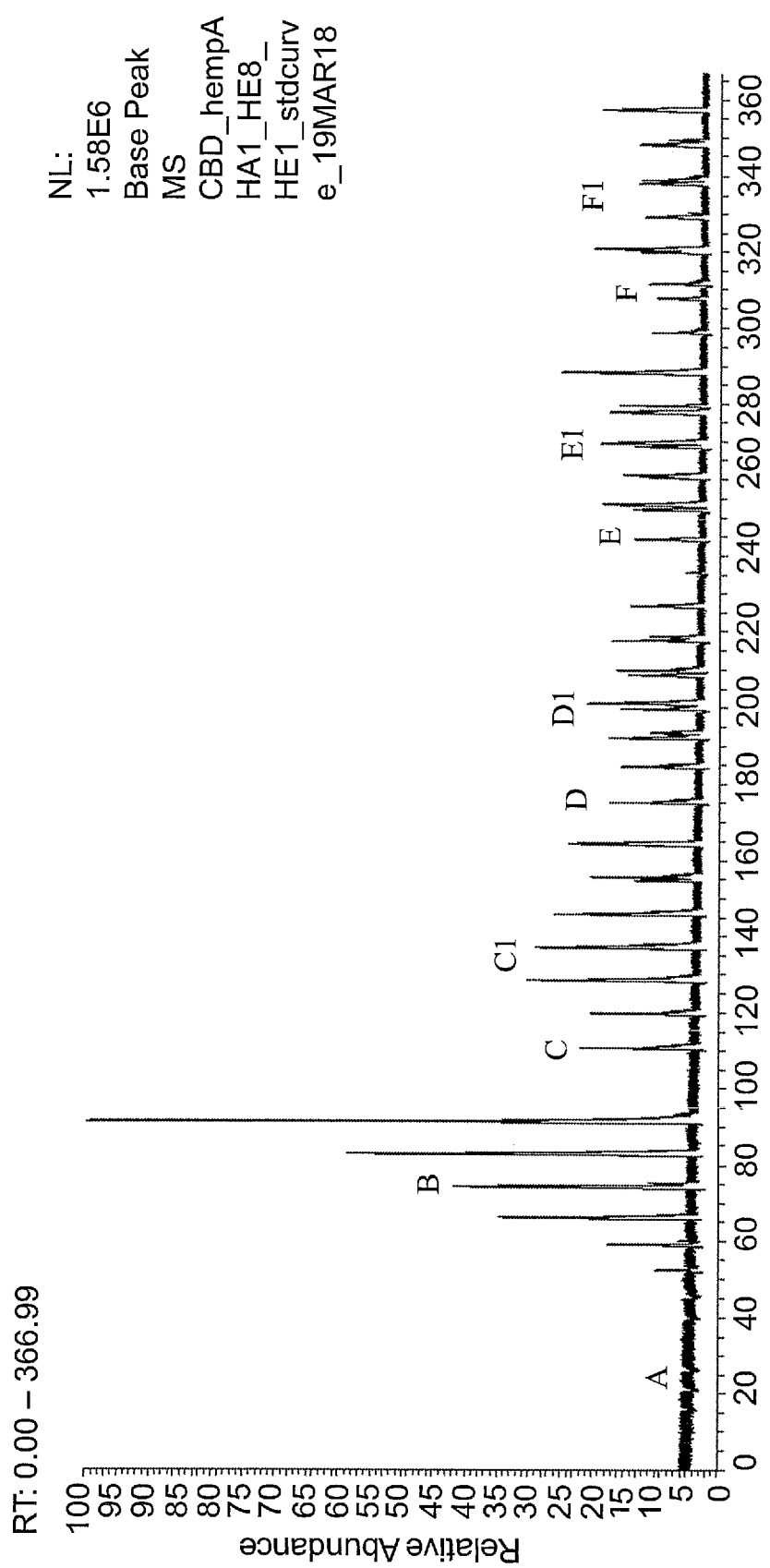
FIG. 3. The separation and detection of CBD in hemp A on a 300 Angstrom 5 micron C18 porous resin by LC-ESI-MS with a isocratic HPLC in 70% AcN 0.1% formic acid of HA1, HE8, and HE1 extract (n=5). Spectra depicts (A) 3× blank (B) external CBD standard curve from 0-200 uM (C) detection of CBD (m/z 315) in hemp A HA1 extract, (D) HE8 extract (E) HE1 extract, (F) mix of HE8 and HE1 extract, (C1) HA1 extract spiked with CBD-D3 (m/z 318), (D1) HE8 extract spiked with CBD-D3, (E1) HE1 extract spiked with CBD-D3 and (F1) mix of HE8 and HE1 extract spiked with CBD-D3. (HA1: sampled heated extracted in 100% can; HE8: sample heated extracted in 80% EtOH; HE1: sample heated extracted in 100% EtOH).

FIG. 3 shows the separation and detection of CBD in hemp sample A on a 300 Angstrom 5 micron C18 porous resin by LC-ESI-MS with a isocratic HPLC in 70% AcN 0.1% formic acid. HA1 is a sample heated and extracted in 100% acetonitrile (AcN); HE8 is a sample heated and extracted in 80% EtOH; and HE1 is a sample heated and extracted in 100% EtOH. (n=5). Spectra depicts (A) 3× blank (B) external CBD standard curve from 0-200 uM (C) detection of CBD (m/z 315) in hemp A HA1 extract, (D) HE8 extract (E) HE1 extract, (F) mix of HE8 and HE1 extract, (C1) HA1 extract spiked with CBD-D3 (m/z 318), (D1) HE8 extract spiked with CBD-D3, (E1) HE1 extract spiked with CBD-D3 and (F1) mix of HE8 and HE1 extract spiked with CBD-D3.

FIG. 4 shows the separation and detection of CBD, CBDa, THC and THCa by isocratic HPLC in 70% AcN 0.1% formic acid and LC-ESI-MS (n=1), using a Kinetex™ coreshell resin.

Figure 4A:
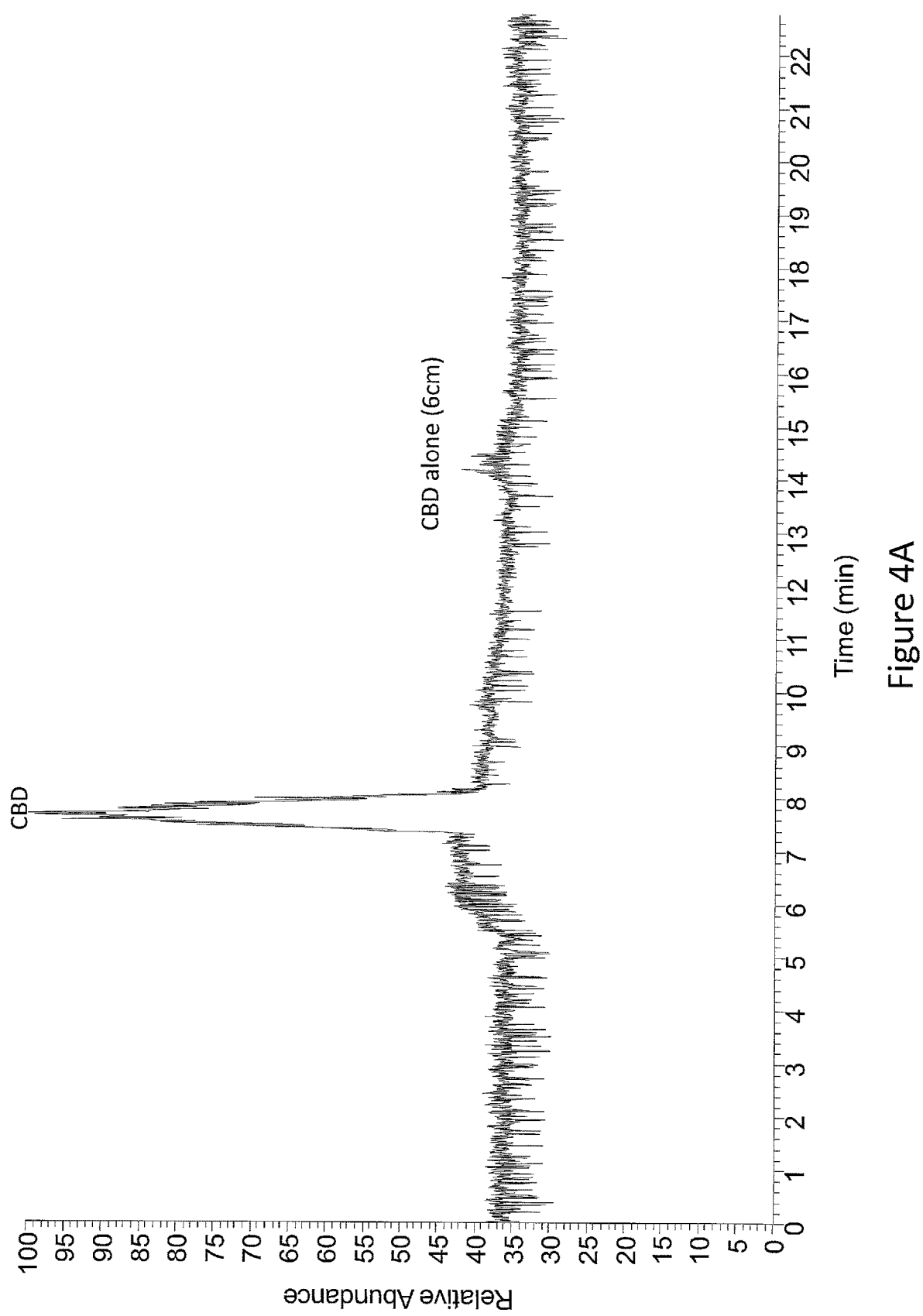
FIG. 4A. The separation and detection of CBD alone by isocratic HPLC in 70% AcN 0.1% formic acid and LC-ESI-MS (n=1), on a 6 cm column, using a Kinetex™ coreshell resin.
Figure 4B:
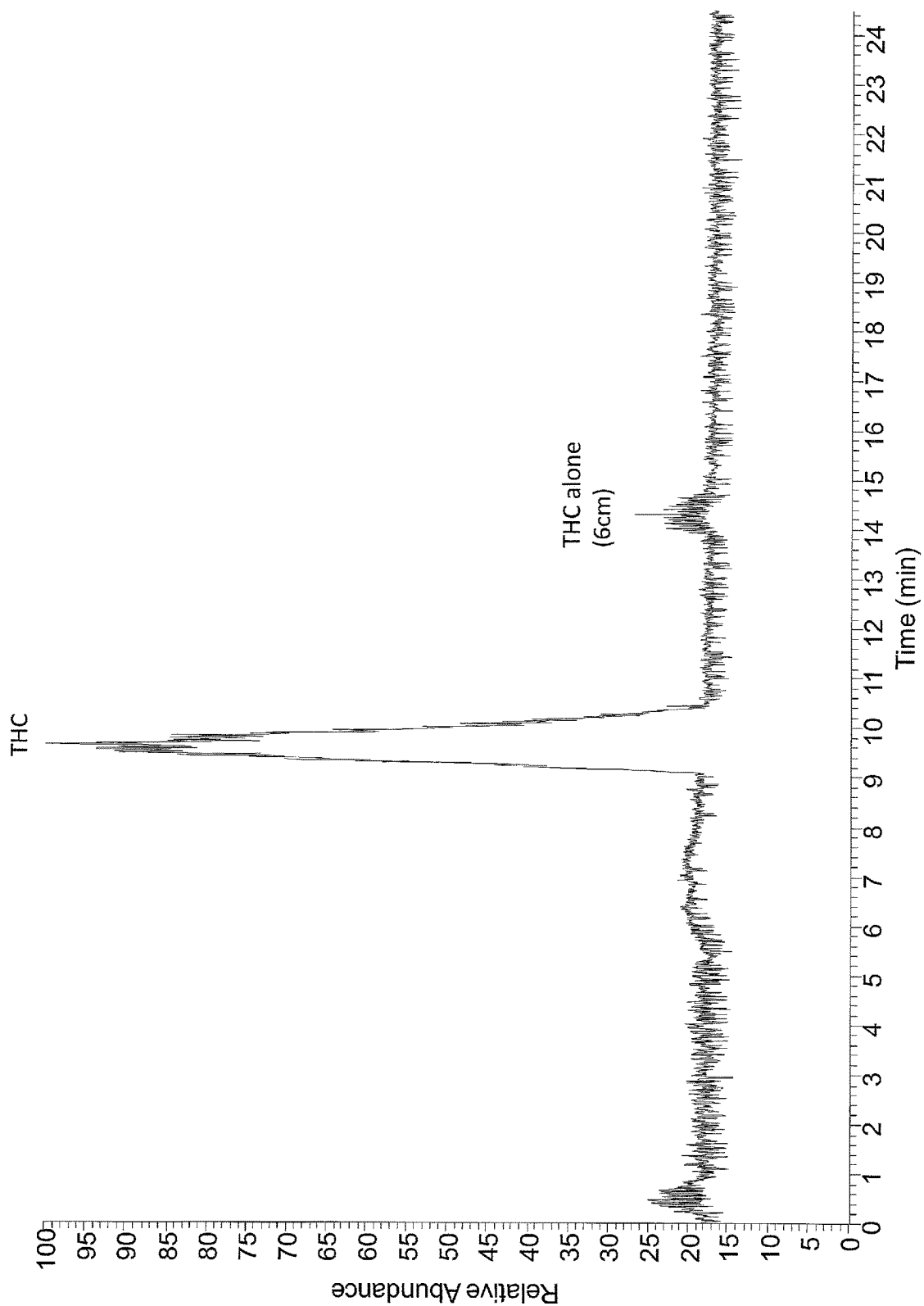
FIG. 4B. The separation and detection of THC alone by isocratic HPLC in 70% AcN 0.1% formic acid and LC-ESI-MS (n=1), on a 6 cm column, using a Kinetex™ coreshell resin.
Figure 4C:
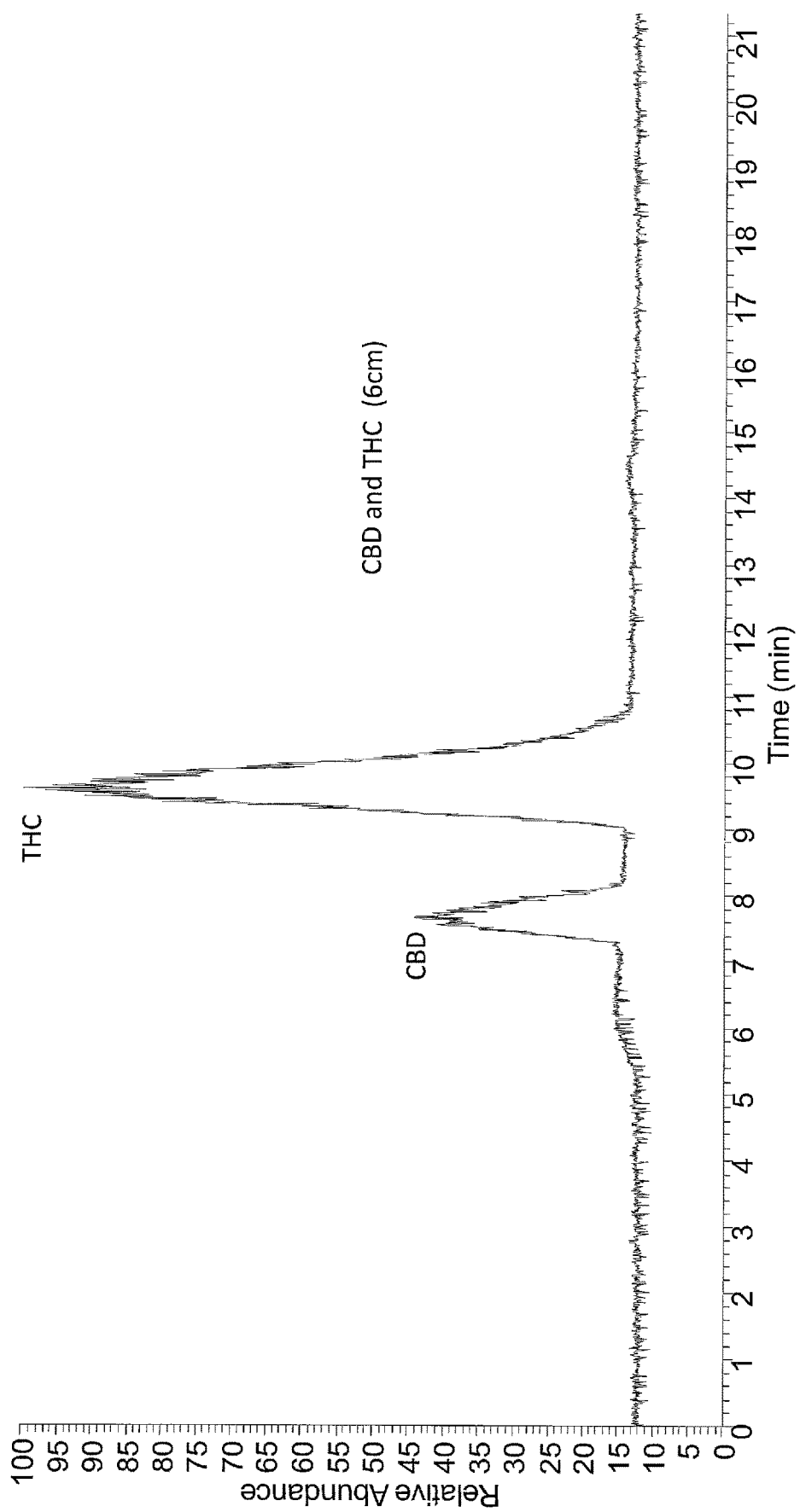
FIG. 4C. The separation and detection of CBD and THC by isocratic HPLC in 70% AcN 0.1% formic acid and LC-ESI-MS (n=1), on a 6 cm column, using a Kinetex™ coreshell resin.
Figure 4D:
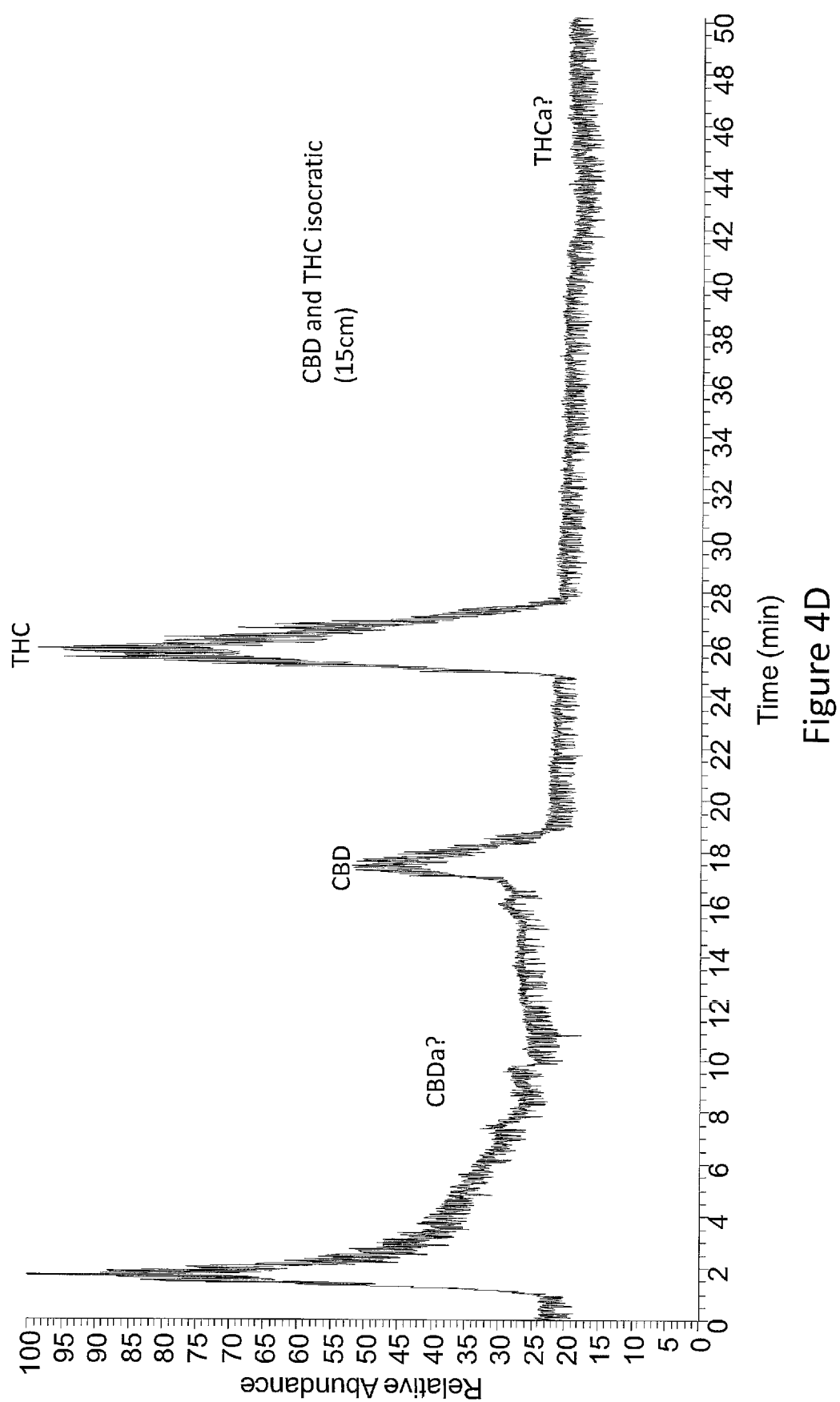
FIG. 4D. The separation and detection of CBD and THC by isocratic HPLC in 70% AcN 0.1% formic acid and LC-ESI-MS (n=1), on a 15 cm column, using a Kinetex™ coreshell resin.

FIG. 4A—CBD alone;
FIG. 4B—THC alone;
FIG. 4C—CBD and THC separation on a 6 cm column;
FIG. 4D, CBD and THC separation on a 15 cm column.

Figure 5A:
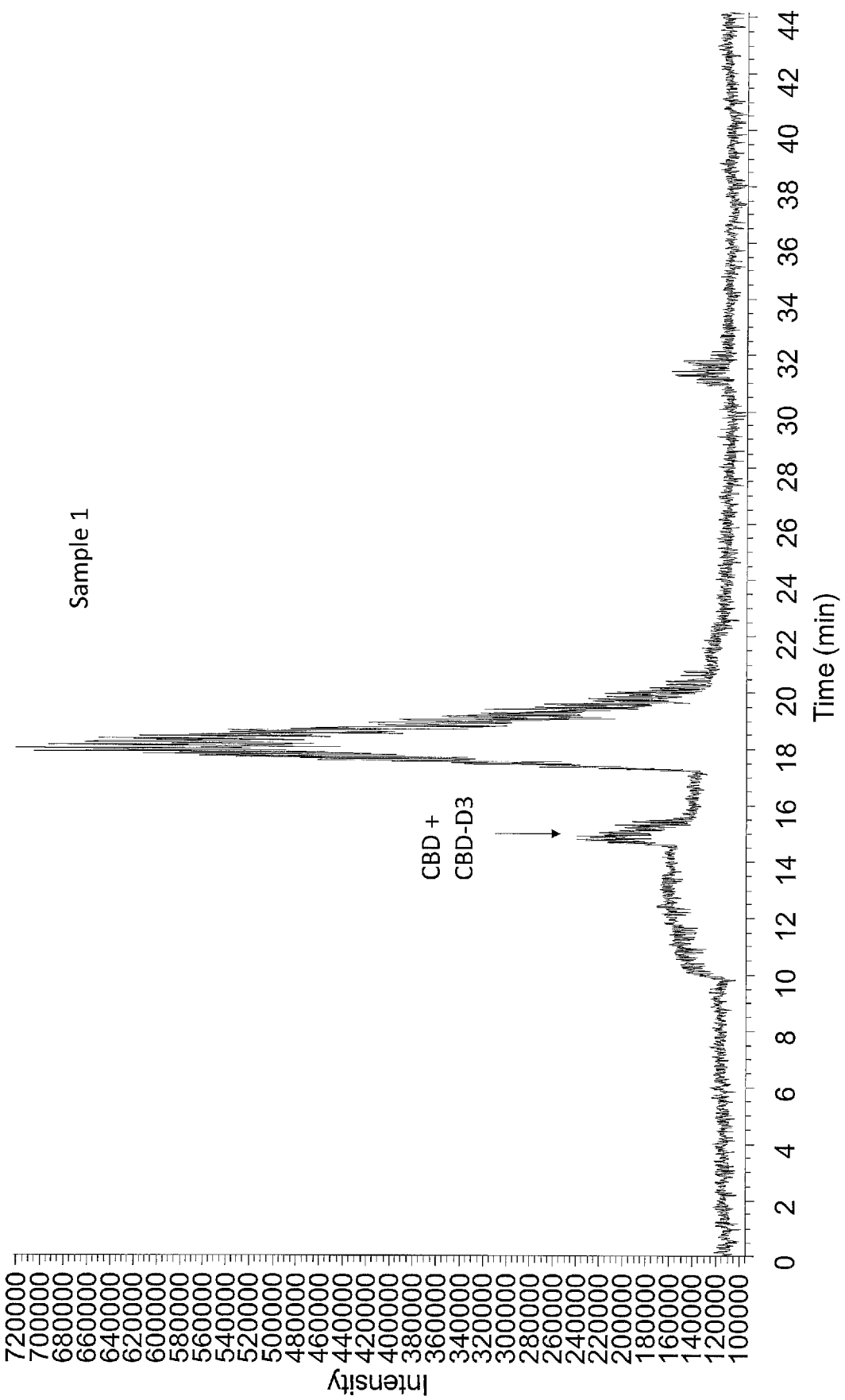
FIG. 5A. The separation and detection of CBD, CBDa, THC and THCa by gradient HPLC and LC-ESI-MS (n=1), for Sample 1 spiked with CBD-D3Gradients—Sample was diluted in B buffer (65% AcN, 5% FA) with gradient 0 min at 70%, 10 min linear gradient to 80%, held for 5 min at 80% and equilibrate at 70% (base peak).
Figure 5B:
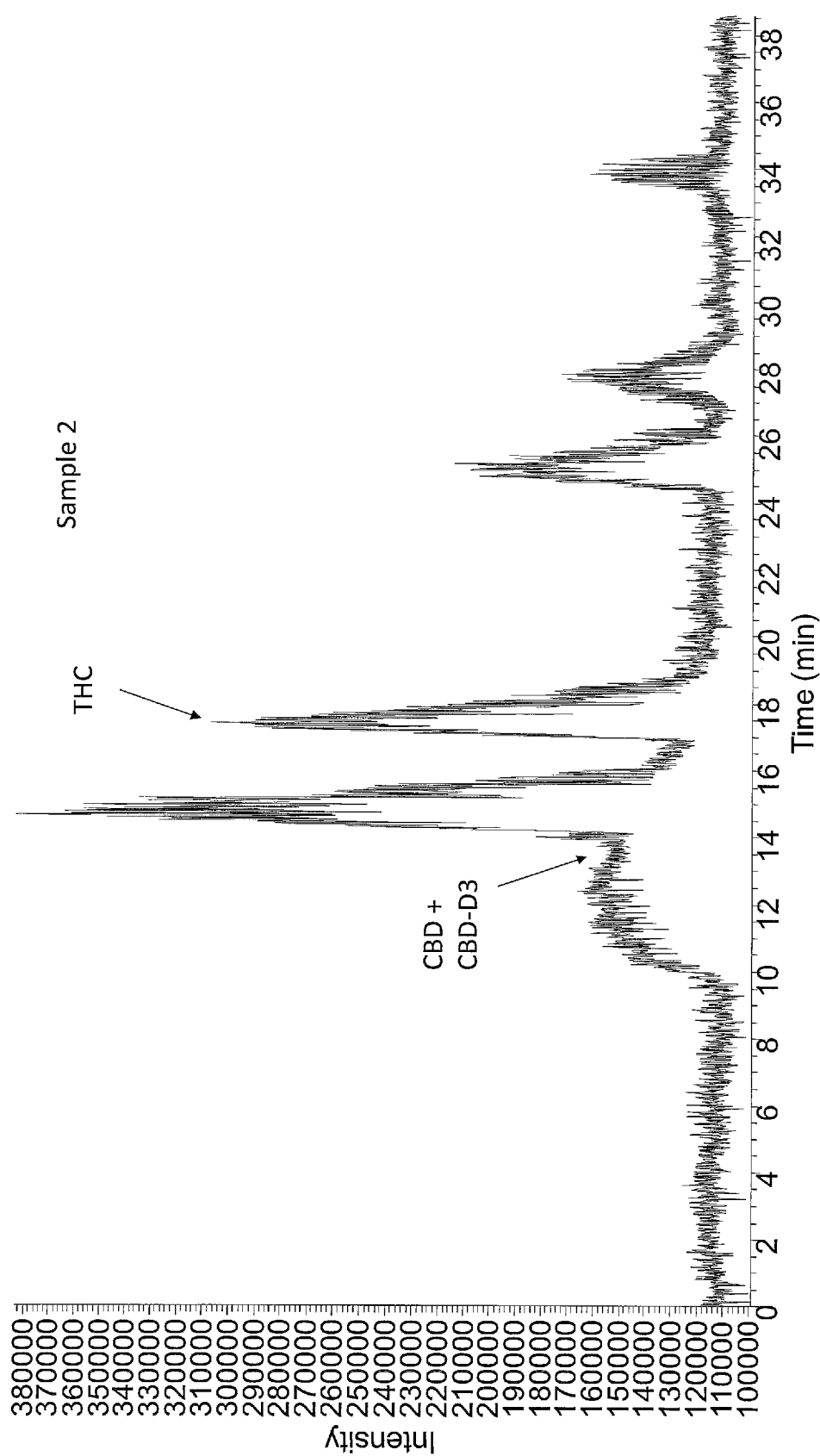
FIG. 5B. The separation and detection of CBD, CBDa, THC and THCa by gradient HPLC and LC-ESI-MS (n=1) for Sample 2 spiked with CBD-D3. Gradients—Sample was diluted in B buffer (65% AcN, 5% FA) with gradient 0 min at 70%, 10 min linear gradient to 80%, held for 5 min at 80% and equilibrate at 70% (base peak).
Figure 5C:
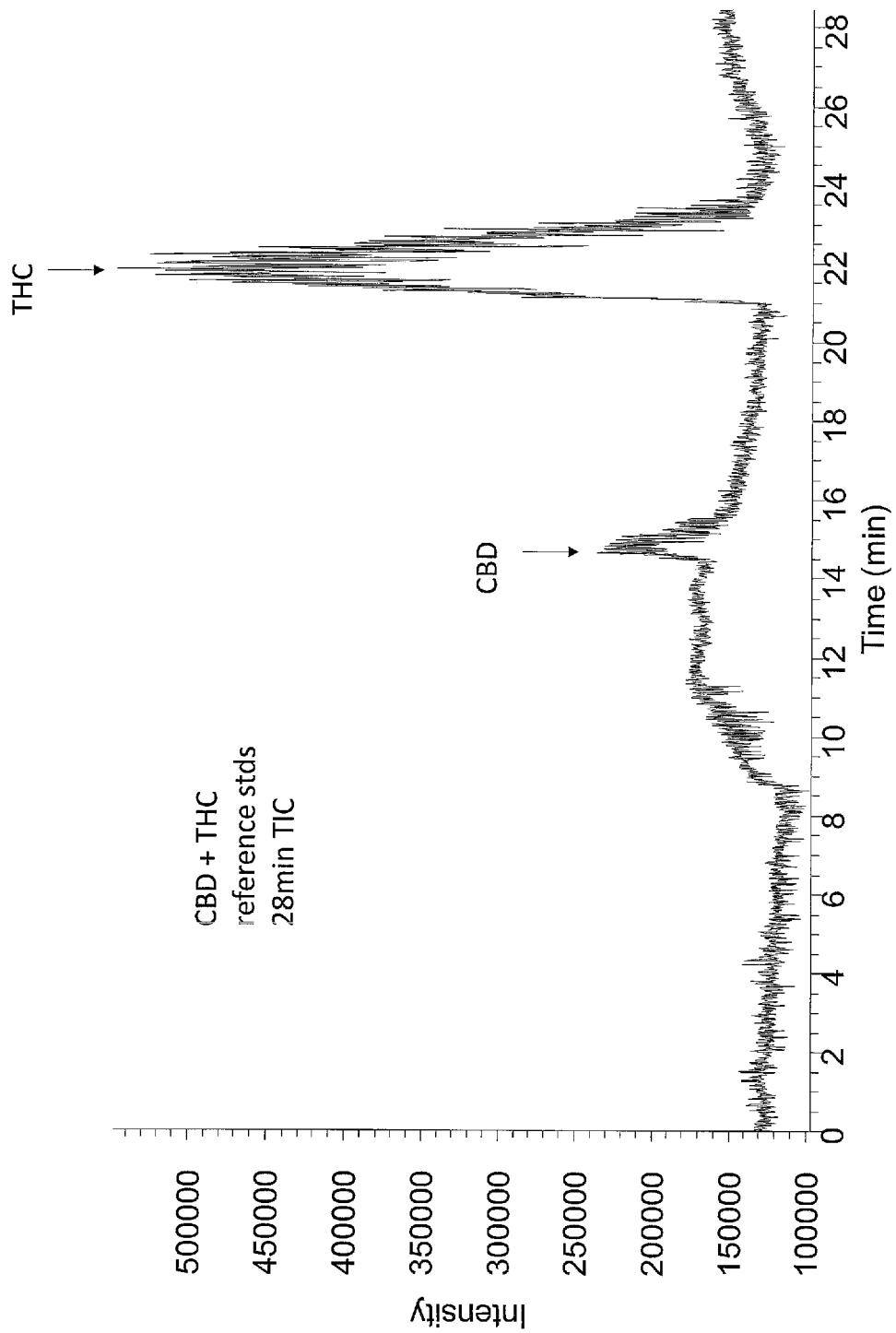
FIG. 5C. The separation and detection of CBD, CBDa, THC and THCa by gradient HPLC and LC-ESI-MS (n=1) for CBD and THC reference standards. Gradients—Sample was diluted in B buffer (65% AcN, 5% FA) with gradient 0 min at 70%, 10 min linear gradient to 80%, held for 5 min at 80% and equilibrate at 70% (base peak).
Figure 5D:
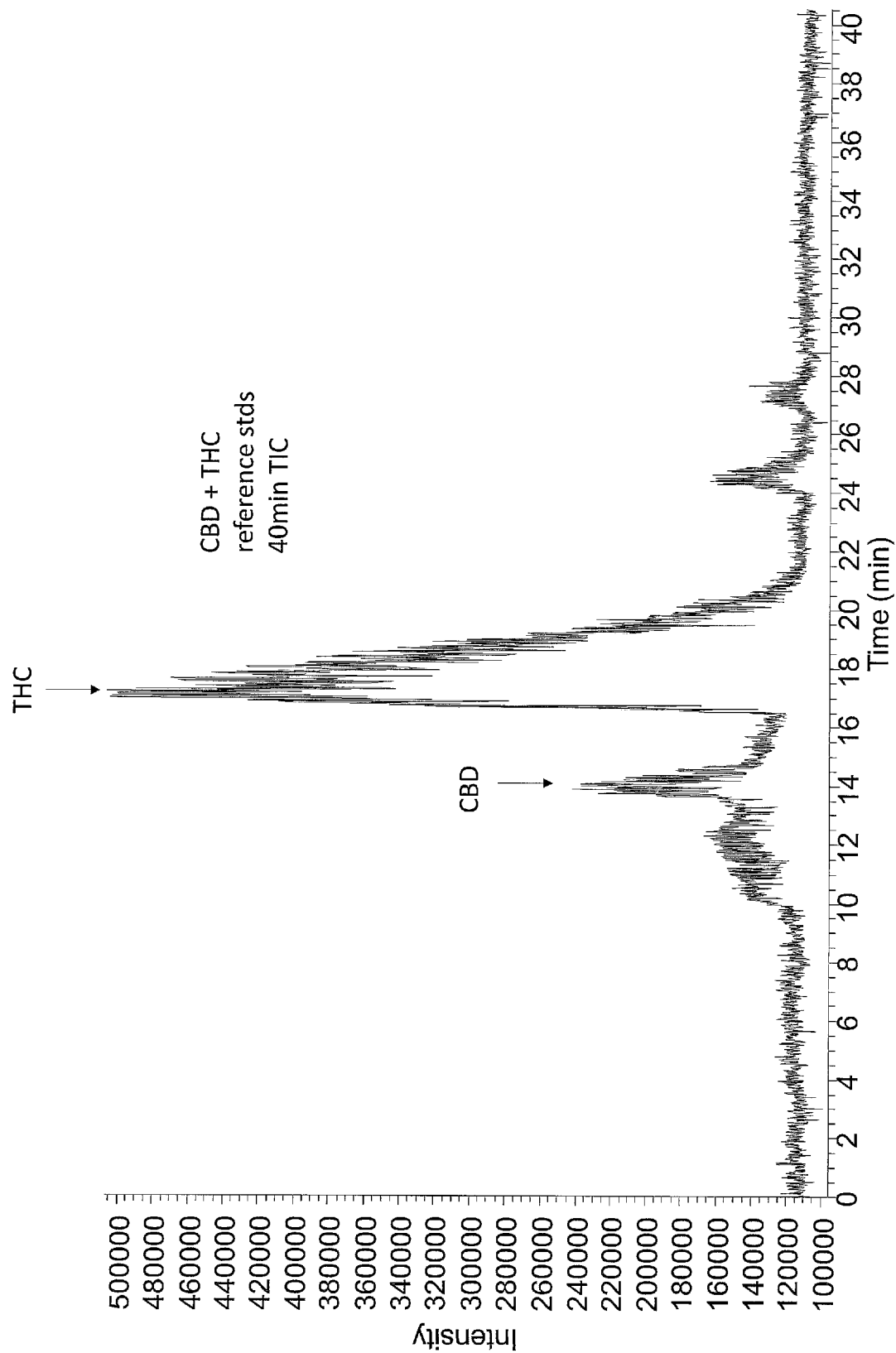
FIG. 5D. The separation and detection of CBD, CBDa, THC and THCa by gradient HPLC and LC-ESI-MS (n=1) for CBD and THC reference standards. Gradients—Sample was diluted in B buffer (65% AcN, 5% FA) with gradient 0 min at 70%, 10 min linear gradient to 80%, held for 5 min at 80% and equilibrate at 70% (base peak).
Figure 6A:
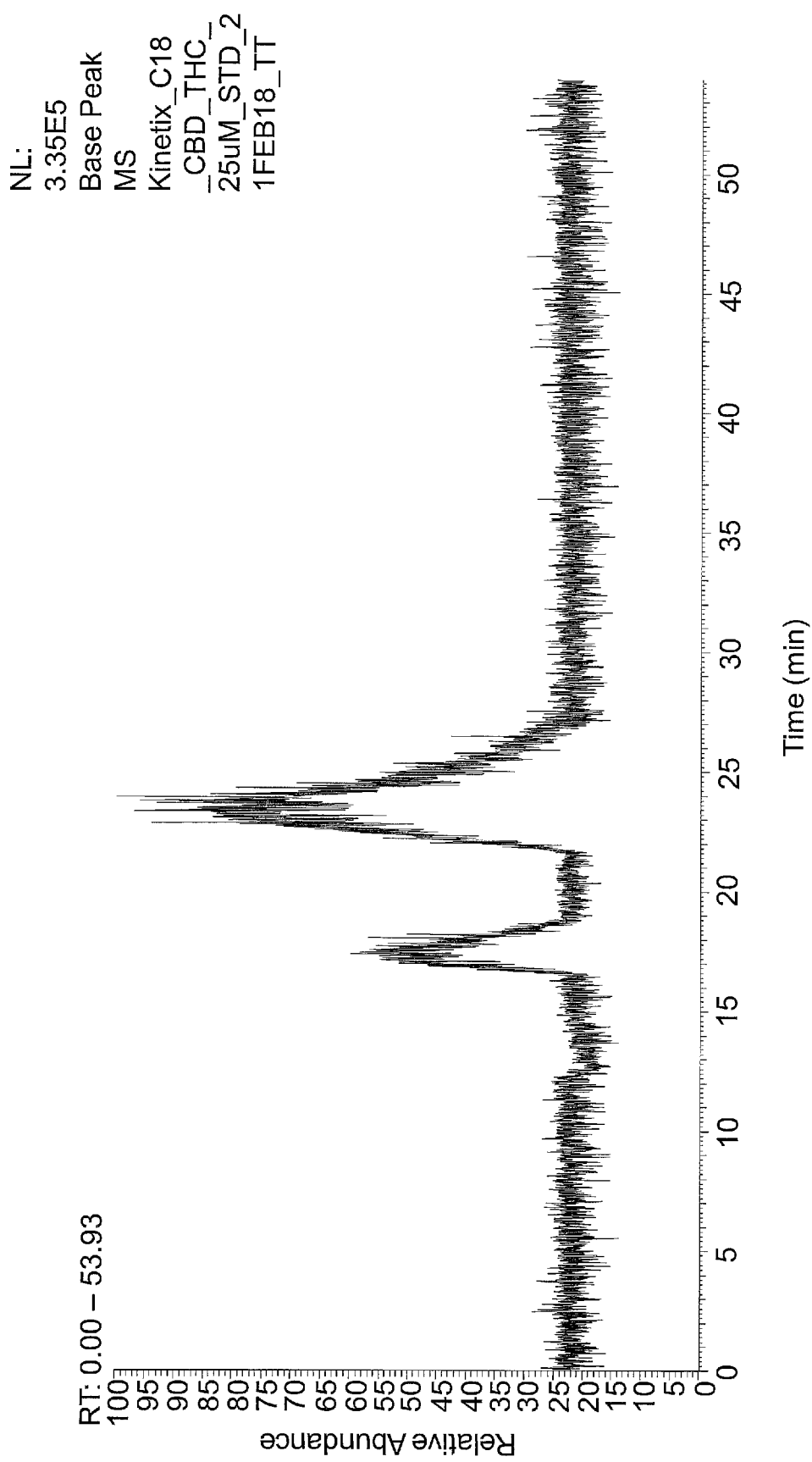
FIG. 6A. The separation and detection of CBD, CBDa, THC and THCa by isocratic HPLC in 70% AcN 0.1% formic acid and LC-ESI-MS (n=1) on a 15 cm column over Kinetex™ coreshell resin for CBD and THC reference standard.
Figure 6B:
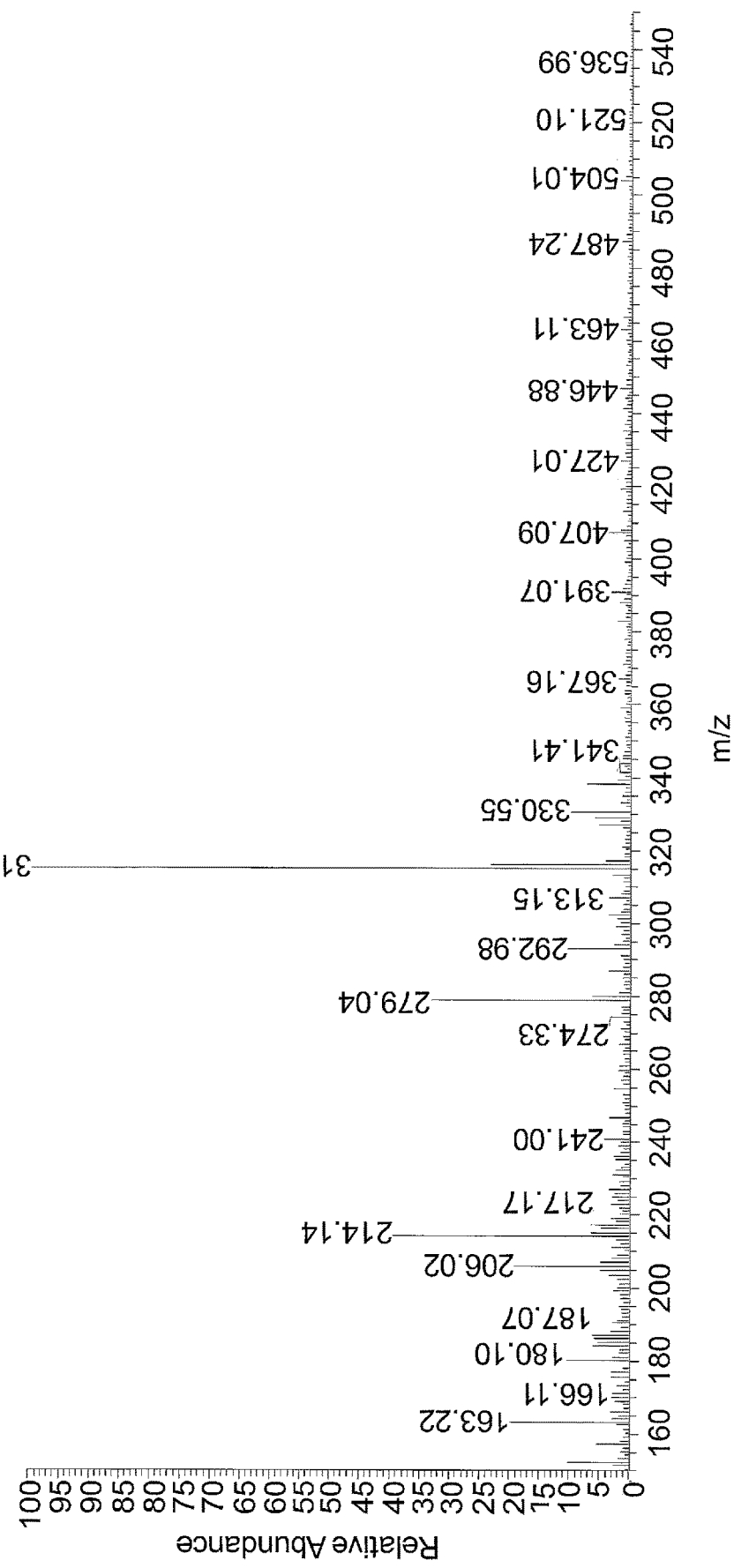
FIG. 6B. The separation and detection of CBD, CBDa, THC and THCa by isocratic HPLC in 70% AcN 0.1% formic acid and LC-ESI-MS (n=1) on a 15 cm column over Kinetex™ coreshell resin for CBD alone.
Figure 6C:
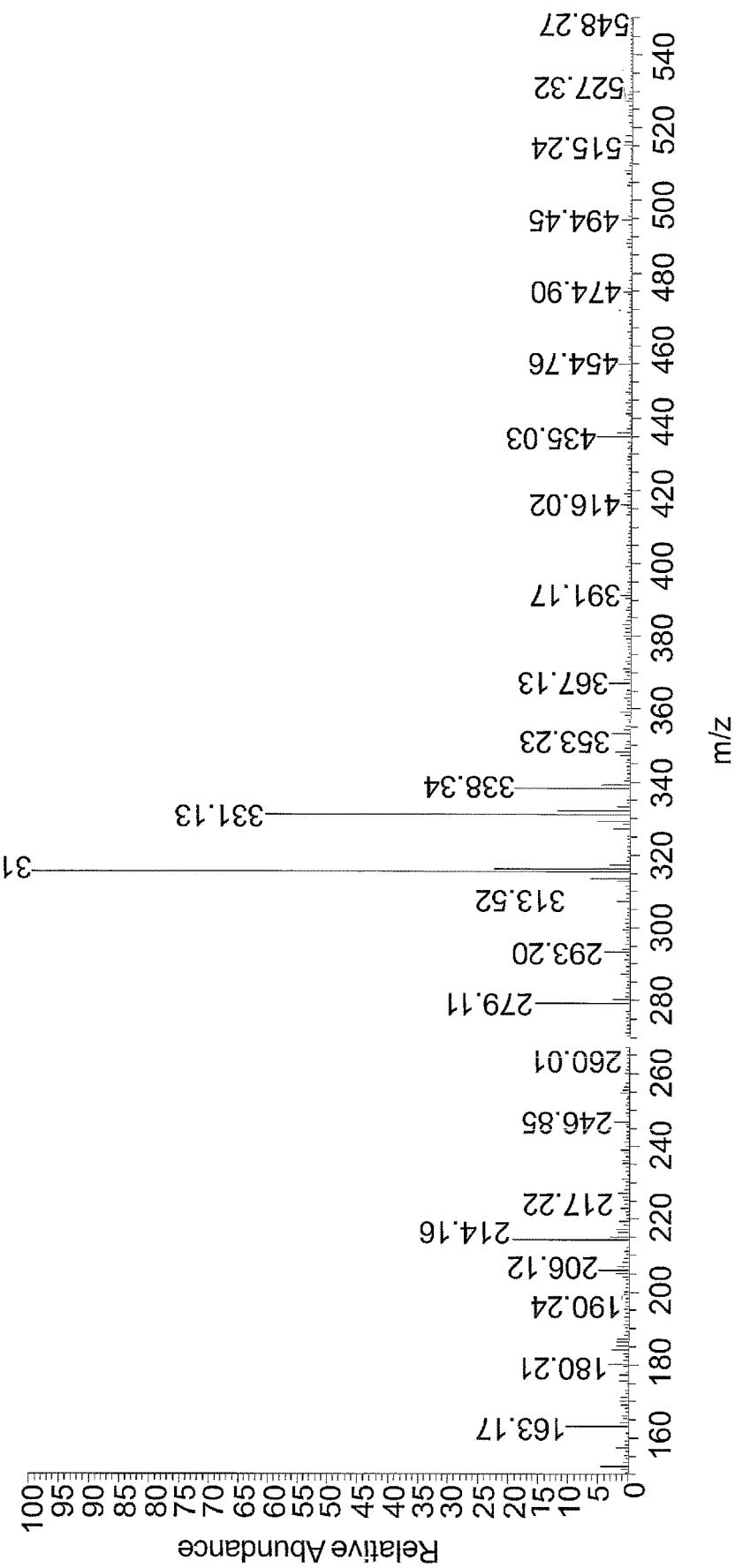
FIG. 6C. The separation and detection of CBD, CBDa, THC and THCa by isocratic HPLC in 70% AcN 0.1% formic acid and LC-ESI-MS (n=1) on a 15 cm column over Kinetex™ coreshell resin for THC alone.
Figure 6D:
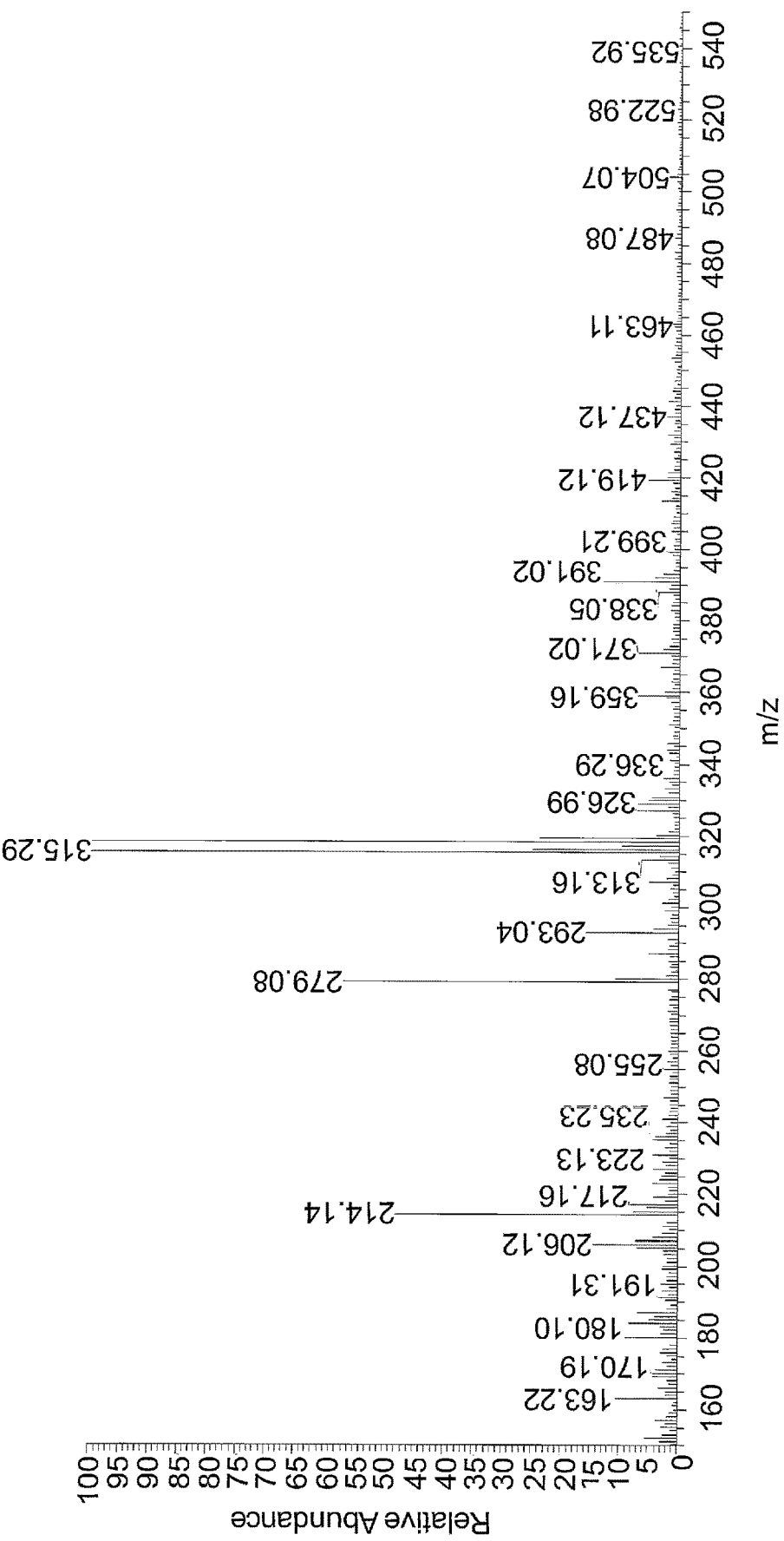
FIG. 6D. The separation and detection of CBD, CBDa, THC and THCa by isocratic HPLC in 70% AcN 0.1% formic acid and LC-ESI-MS (n=1) on a 15 cm column over Kinetex™ coreshell resin for Sample A spiked with CBD-D3.
Figure 6E:
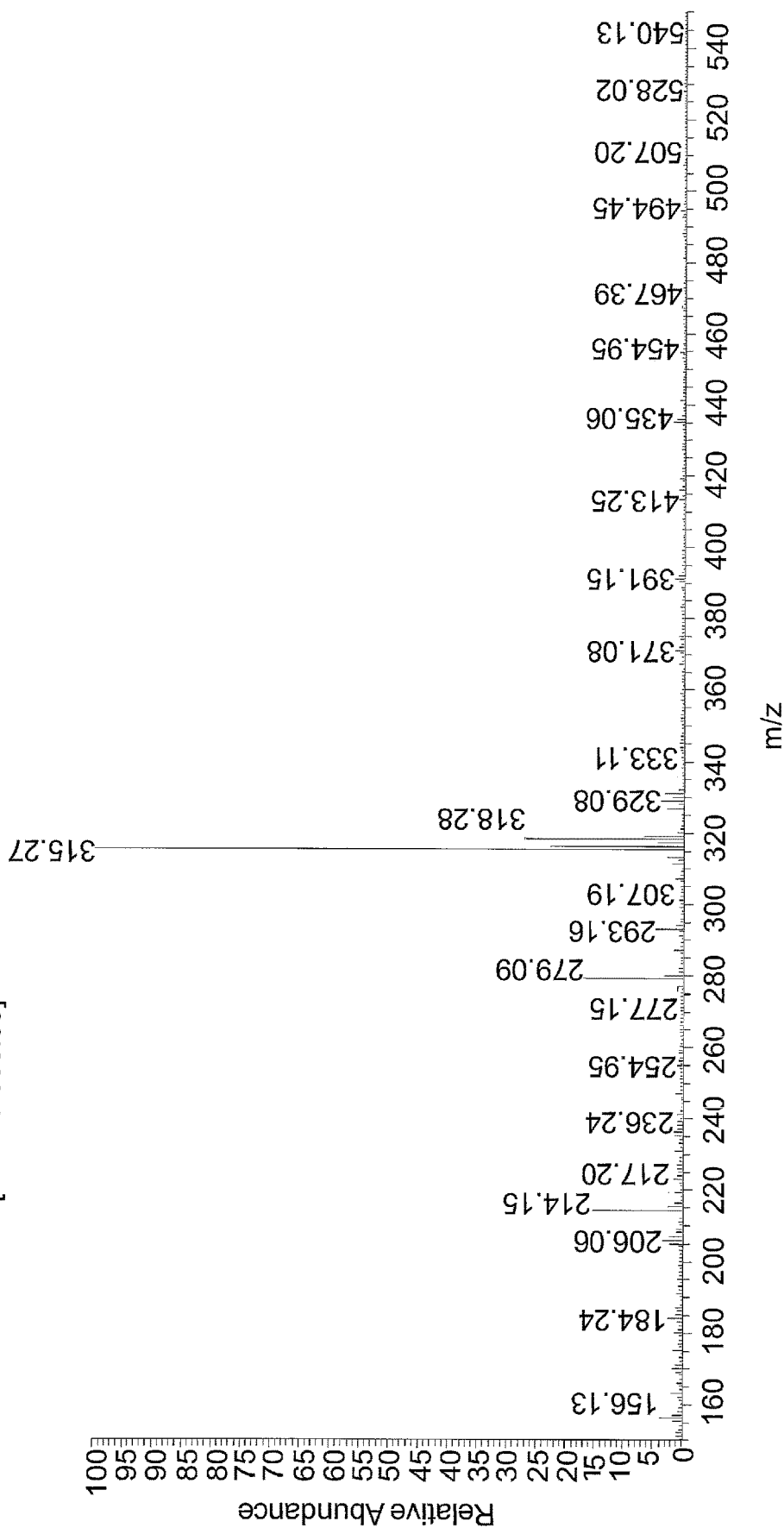
FIG. 6E. The separation and detection of CBD, CBDa, THC and THCa by isocratic HPLC in 70% AcN 0.1% formic acid and LC-ESI-MS (n=1) on a 15 cm column over Kinetex™ coreshell resin for Sample B spiked with THC-D3.

FIGS. 5A and 5B shows the separation and detection of CBD, CBDa, THC and THCa by gradient HPLC and LC-ESI-MS (n=1). FIG. 5A shows the results for Sample 1 spiked with CBD-D3; and FIG. 5B shows the results for Sample 2 spiked with CBD-D3; FIGS. 5C and 5D show CBD and THC reference standards respectively. Gradients—Samples were diluted in B buffer (65% AcN, 5% FA) with gradient 0 min at 70%, 10 min linear gradient to 80%, held for 5 min at 80% and equilibrate at 70% (base peak).

FIG. 6 shows the separation and detection of CBD, CBDa, THC and THCa by isocratic HPLC in 70% AcN 0.1% formic acid and LC-ESI-MS (n=1) on a 15 cm column over Kinetex™ coreshell resin. FIG. 6A shows the CBD and THC reference standard; 6B shows CBD alone; 6C shows THC alone; 6D shows sample A spiked with CBD-D3; 6E shows sample B spiked with THC-D3.

Figure 7A:
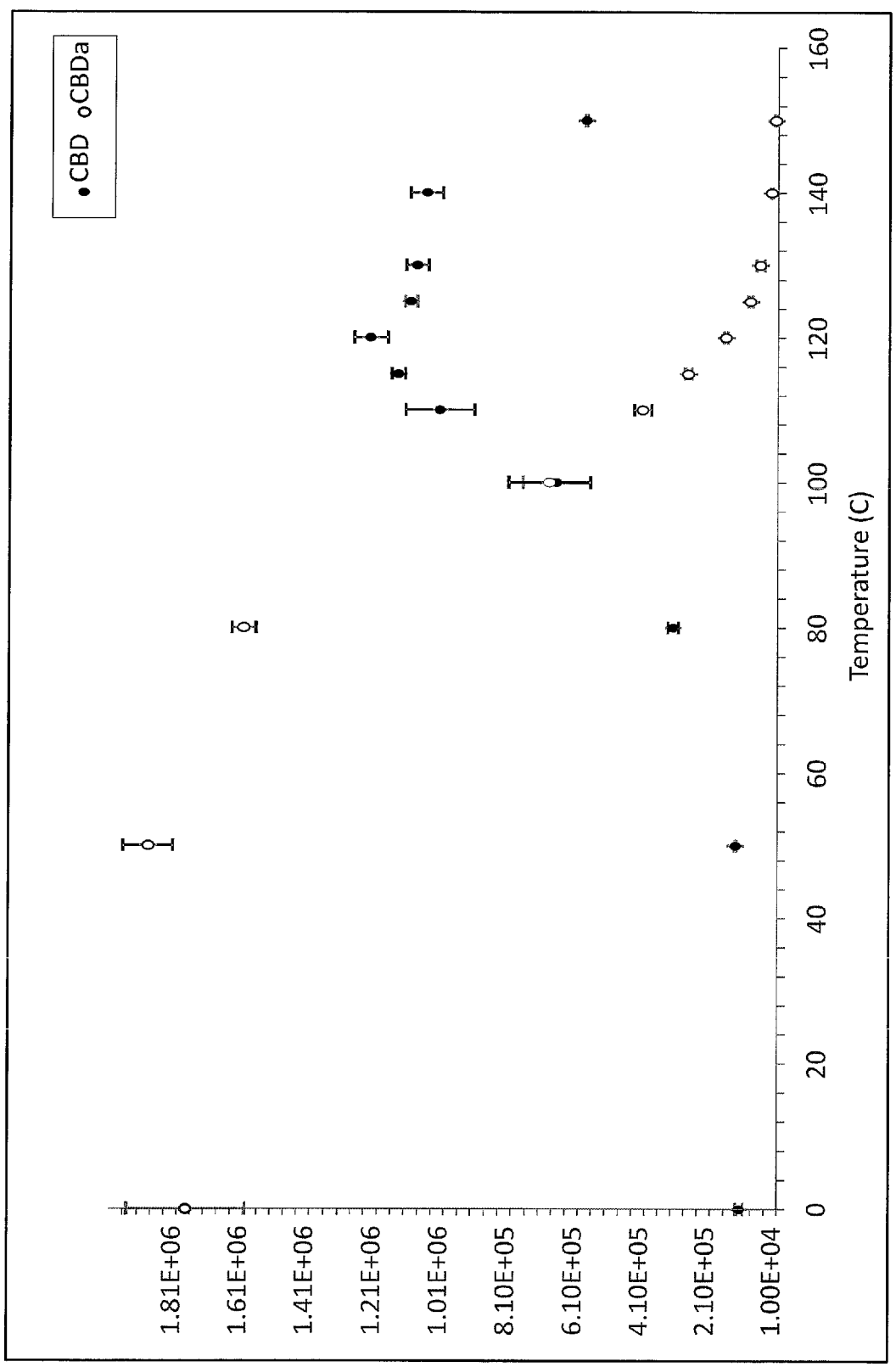
FIG. 7A. Decarboxylation of CBDa at different temperatures for 0.1 g of hemp sample 1 heated to the appropriate temperature for 1 hour and extracted 3× with 100% Ethanol prior to LC-ESI-MS (n=3).
Figure 7B:
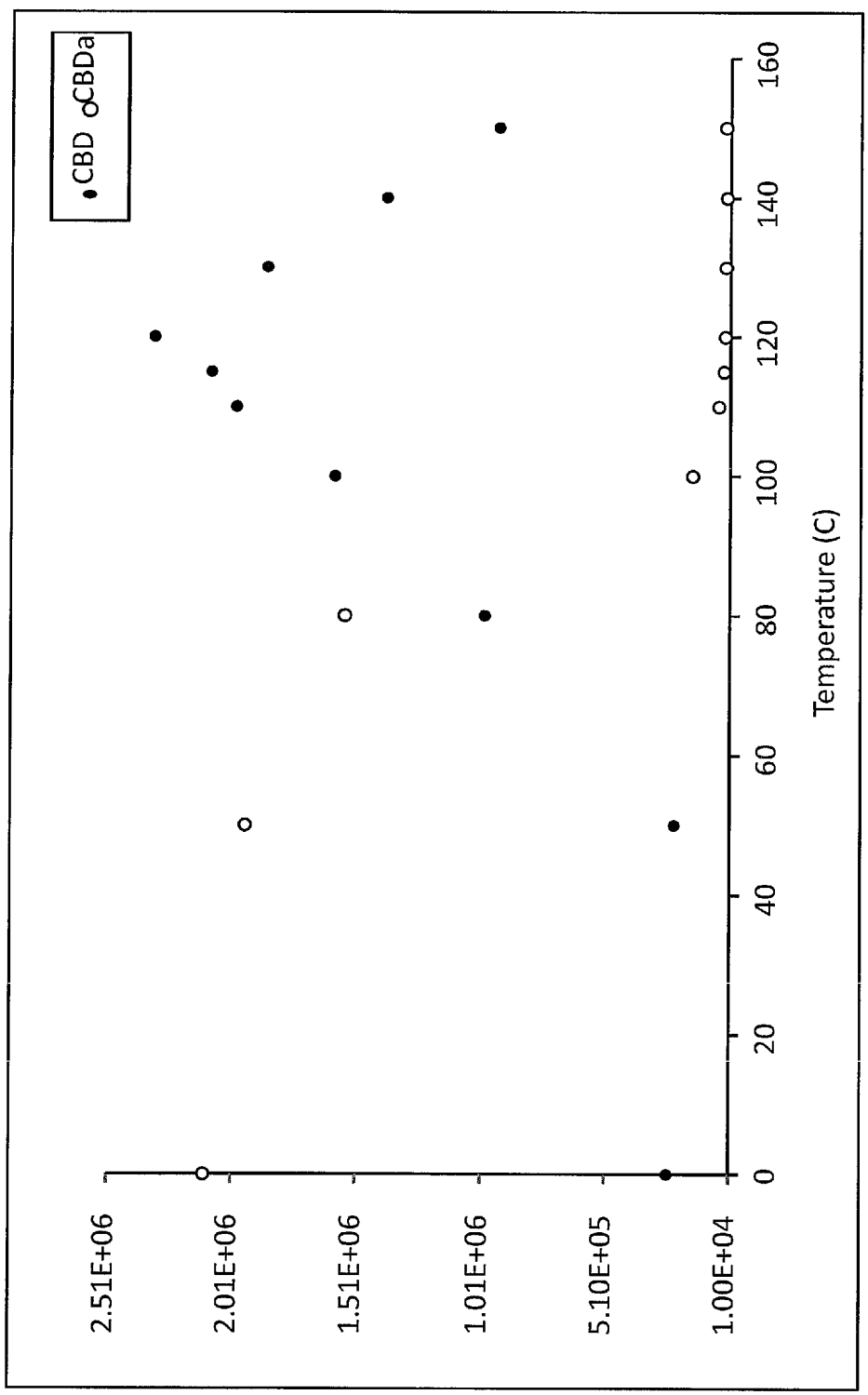
FIG. 7B. Decarboxylation of CBDa at different temperatures for 0.1 g of hemp sample 2 heated to the appropriate temperature for 1 hour and extracted with 100% Ethanol prior to LC-ESI-MS (n=1).
Figure 7C:
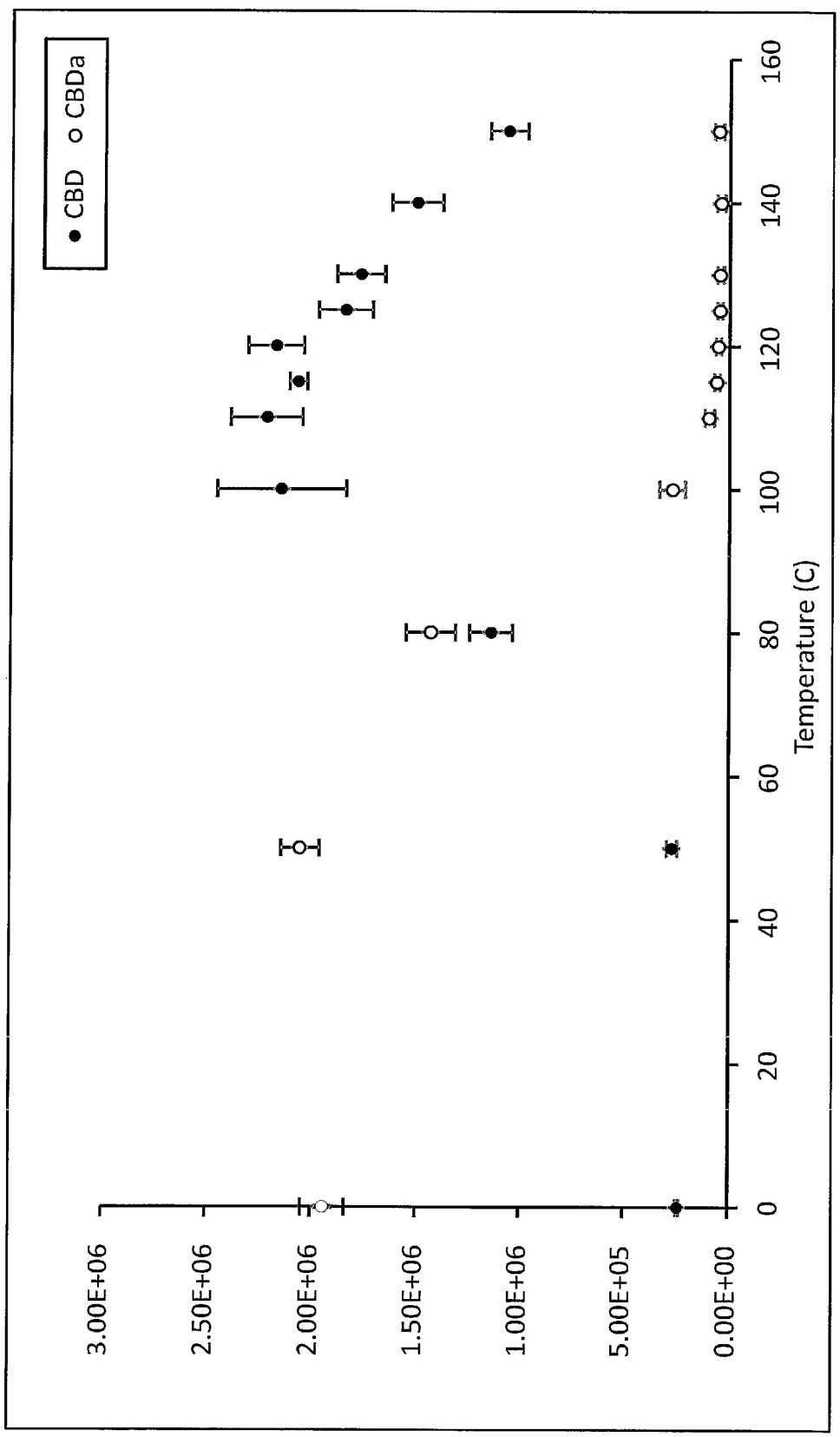
FIG. 7C. Decarboxylation of CBDa at different temperatures for 0.1 g of hemp sample 2 heated to the appropriate temperature for 1 hour and extracted with 100% Ethanol prior to LC-ESI-MS (n=3).

FIG. 7 shows the decarboxylation of CBDa at different temperatures. FIG. 7A, 0.1 g of hemp sample 1 was heated to the appropriate temperature for 1 hour and extracted 3× with 100% Ethanol prior to LC-ESI-MS (n=3); FIG. 7B, 0.1 g of hemp sample 2 was heated to the appropriate temperature for 1 hour and extracted with 100% Ethanol prior to LC-ESI-MS (n=1); FIG. 7C, 0.1 g of hemp sample 2 was heated to the appropriate temperature for 1 hour and extracted with 100% Ethanol prior to LC-ESI-MS (n=3)

Figure 8A:
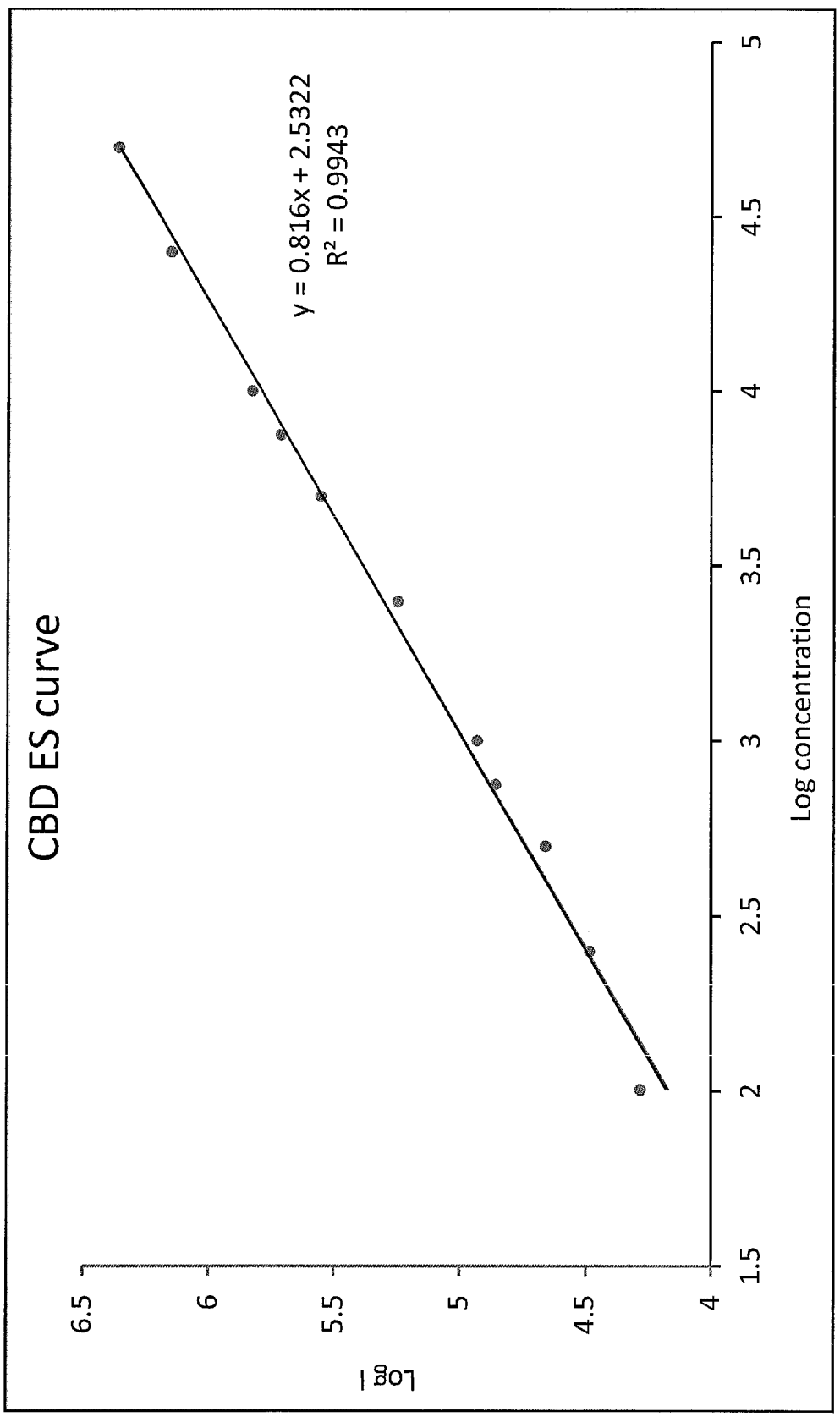
FIG. 8A. CBD external standard curve (n=2) from 50-5000 nM.
Figure 8B:
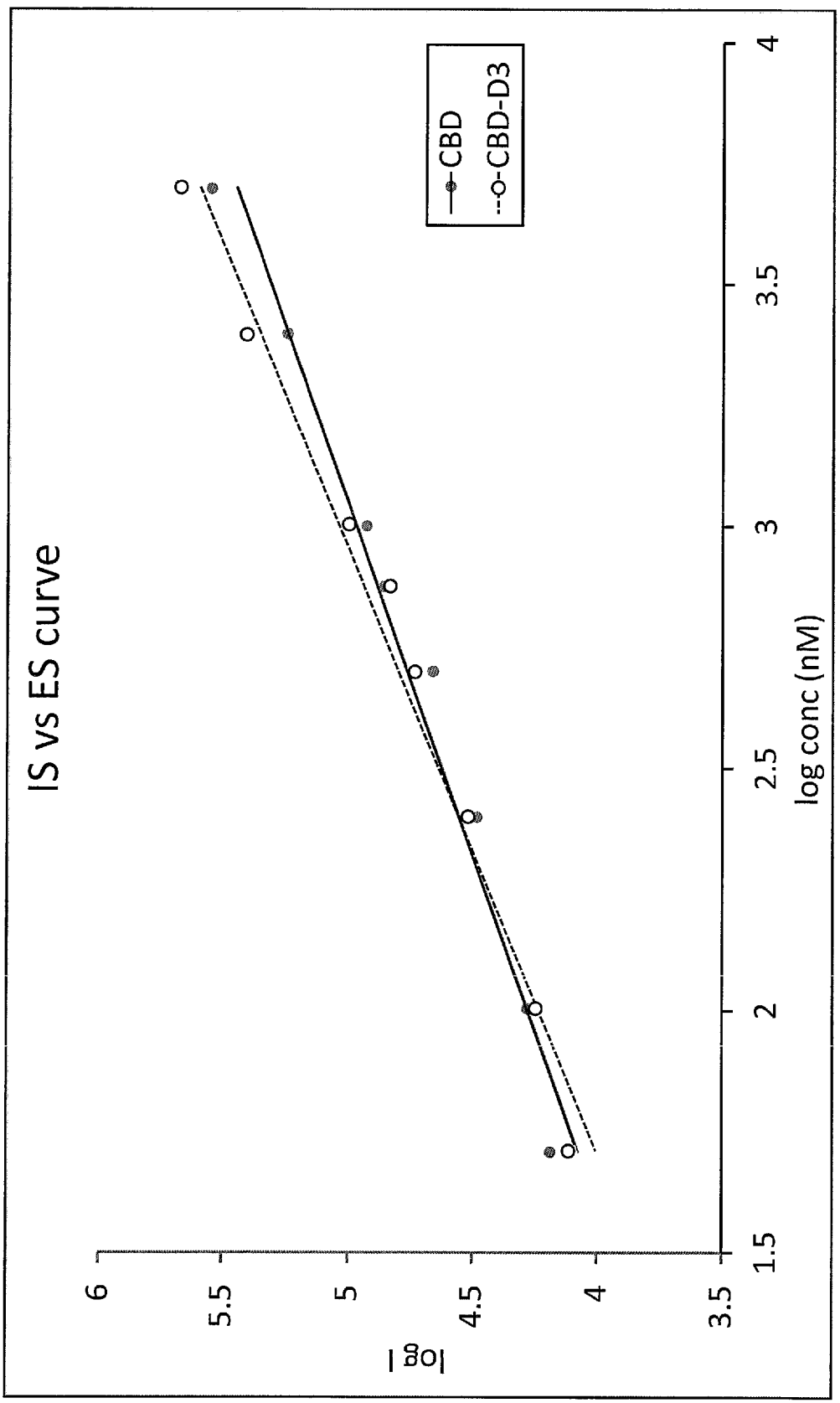
FIG. 8B. Internal versus external CBD curve (n=2) from 50-5000 nM.
Figure 8C:
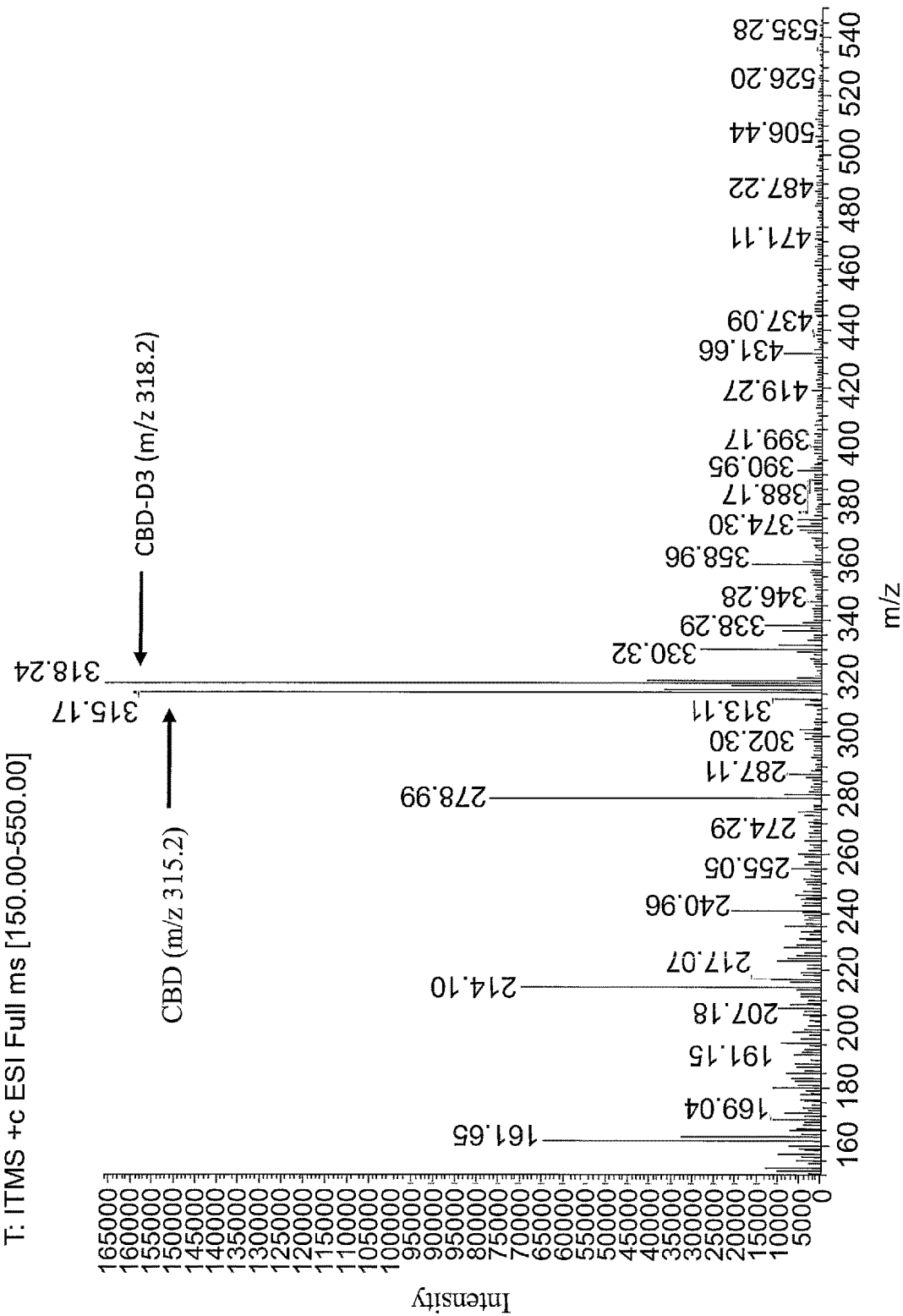
FIG. 8C. Illustration spectra of the detection of CBD (m/z 315) in a hemp sample heated to 120° C. spiked with CBD-D3 (m/z 318) measured by isocratic separation over C18 resin.

FIG. 8 shows a CBD internal vs external standard (ES) curve (n=2) from 50-5000 nM. FIG. 8A shows a CBD external standard curve. FIG. 8B shows an internal versus external CBD curve. FIG. 8C shows an illustration spectra of the detection of CBD (m/z 315) in a hemp sample heated to 120° C. spiked with CBD-D3 (m/z 318) measured by isocratic separation over C18 resin.

Figure 9A:
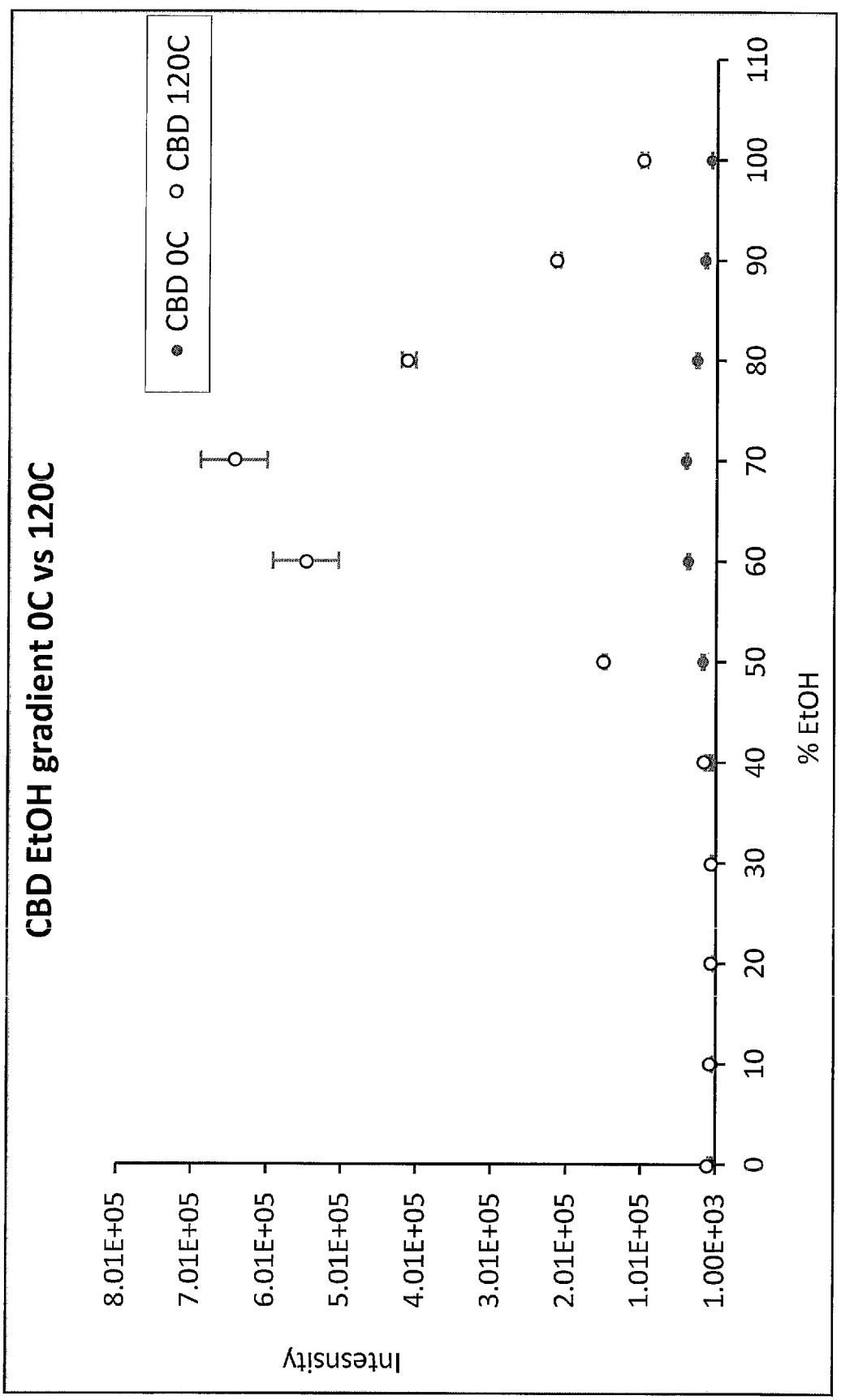
FIG. 9A. EtOH gradient extraction of CBD extracted in ethanol gradient from 0.1 g of hemp heated to 120° C. for 1 hour vs. no heating control (0 C), extracted in a sequential step gradient of increasing Ethanol and analyzed by LC-ESI-MS (n=3).
Figure 9B:
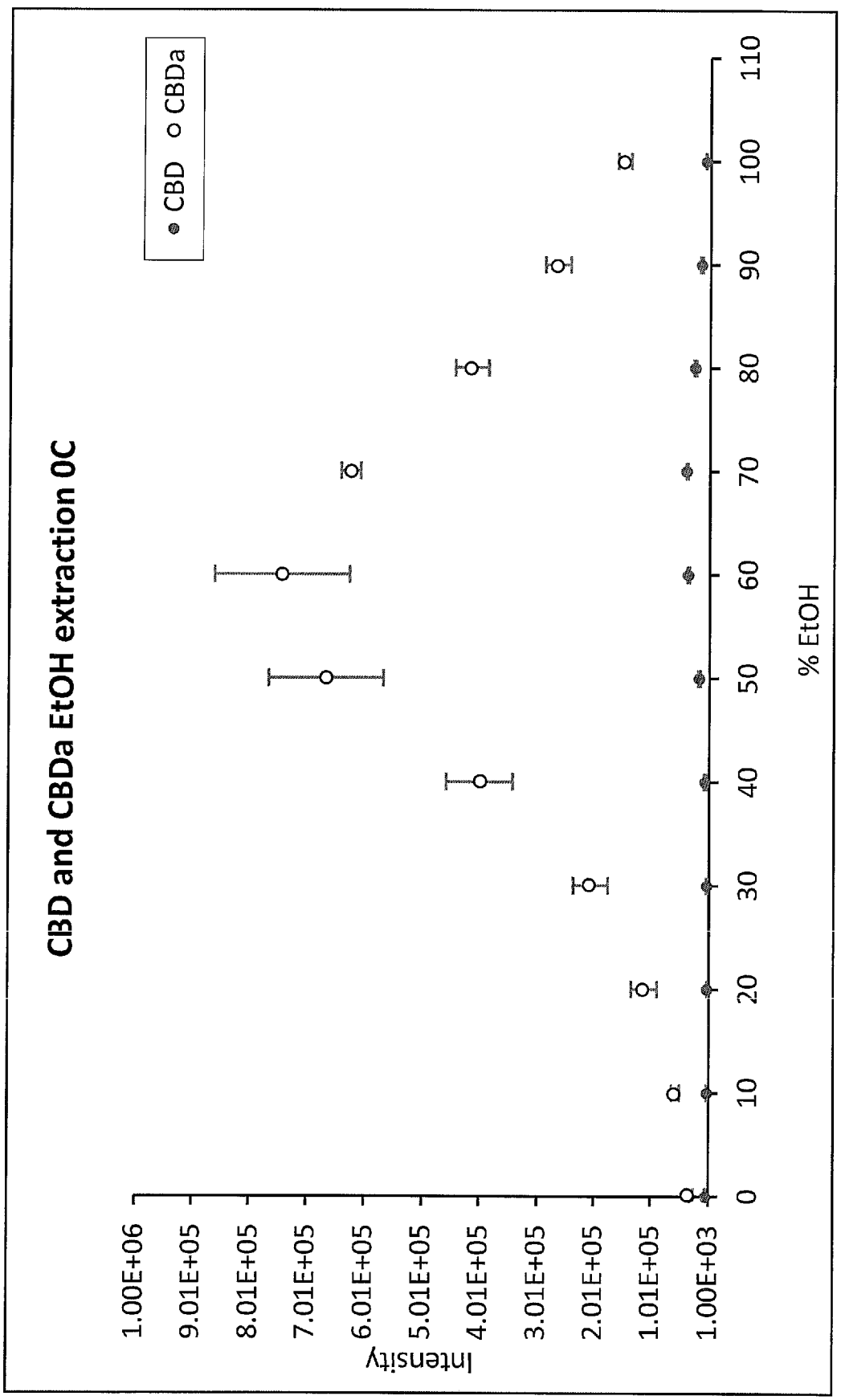
FIG. 9B. EtOH gradient extraction of CBD and CBDa extracted from 0.1 g hemp in an ethanol gradient from the no heating control sample (0 C) and analyzed by LC-ESI-MS (n=3).
Figure 9C:
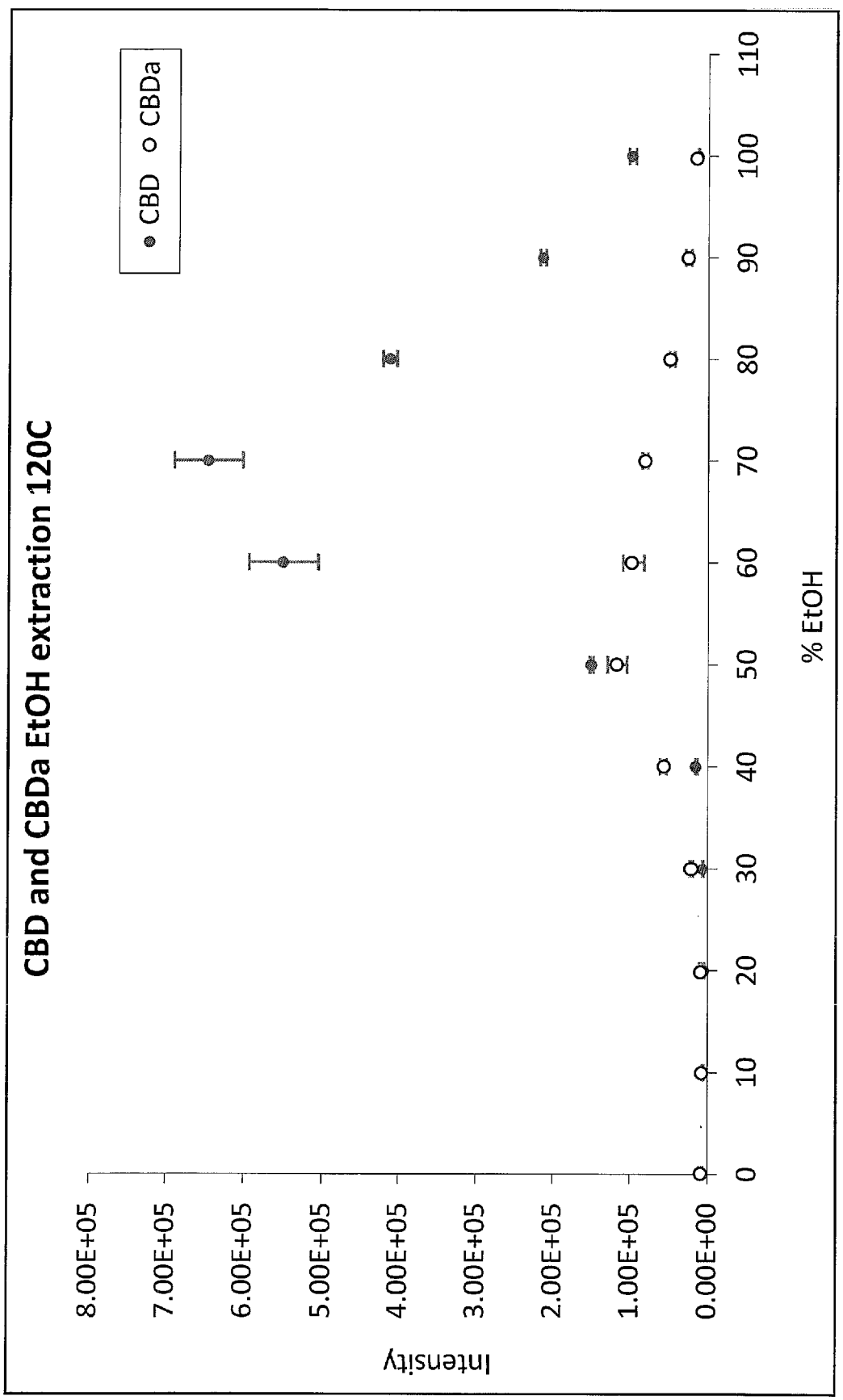
FIG. 9C. EtOH gradient extraction of CBD and CBDa extracted from 0.1 g hemp in an ethanol gradient from a hemp sample heated to 120° C. for 1 hour and analyzed by LC-ESI-MS (n=3).

FIG. 9 shows an EtOH gradient extraction of CBD. 0.1 g of hemp was heated to 120° C. for 1 hour, extracted in a sequential step gradient of increasing Ethanol and analyzed by LC-ESI-MS (n=3). FIG. 9A shows CBD extracted in ethanol gradient from a hemp sample heated to 120° C. vs no heating control (OC); FIG. 9B shows CBD and CBDa extracted in an ethanol gradient (from 0% to 100% vol in water) from the no heating control sample (OC); FIG. 9C shows CBD and CBDa extracted in an ethanol gradient from a hemp sample heated to 120° C. for 1 hour.

Figure 10:
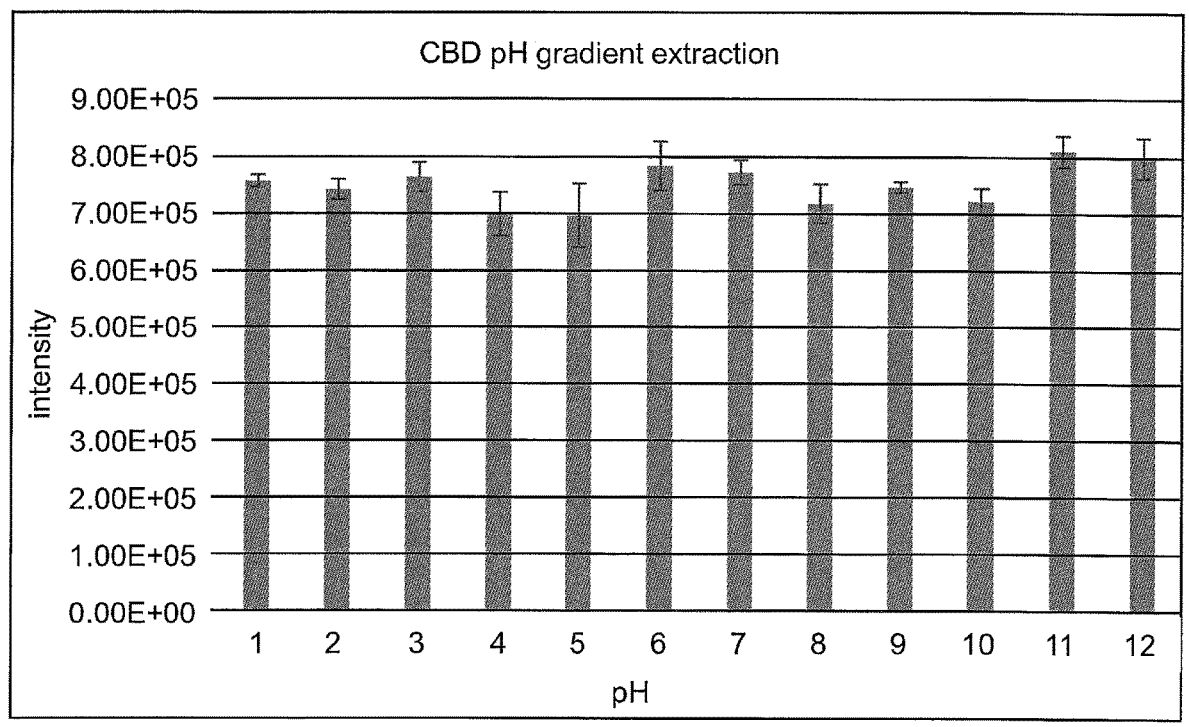
FIG. 10. Effect of pH on the extraction of CBD from hemp in 80% Ethanol (n=3). 0.1 g of hemp was heated to 120° C. for 1 hour, washed 3× with H2O, 3× with 40% Ethanol followed by extraction in 80% Ethanol at various pH levels prior to analysis by LC-ESI-MS. Sample 1, 0.1% TFA in 80% EtOH pH>2 (not adjusted); Sample 2, 0.1% FA in 80% EtOH pH2 (not adjusted); Sample 3, 0.1% Acetic acid in 80% EtOH pH3 (not adjusted); Sample 4, 10 mM Citric acid in 80% EtOH pH4; Sample 5, 10 mM Citrate in 80% EtOH pH5; Sample 6, 10 mM Citrate in 80% EtOH pH6; Sample 7, 10 mM Tris in 80% EtOH pH7; Sample 8, 10 mM Tricine in 80% EtOH pH8; Sample 9, 0.1% Ethanolamine in 80% EtOH pH9; Sample 10, 0.1% Ethanolamine in 80% EtOH pH10; Sample 11, 0.1% Ammonia in 80% EtOH pH<10 (not adjusted); Sample 12, 80% EtOH in H2O (pH not adjusted).

FIG. 10 shows the effect of pH on the extraction of CBD from hemp in 80% Ethanol (n=3). 0.1 g of hemp was heated to 120° C. for 1 hour, washed 3× with H2O, 3× with 40% Ethanol followed by extraction in 80% Ethanol at various pH levels prior to analysis by LC-ESI-MS. Sample 1, 0.1% TFA in 80% EtOH pH>2 (not adjusted); Sample 2, 0.1% FA in 80% EtOH pH2 (not adjusted); Sample 3, 0.1% Acetic acid in 80% EtOH pH3 (not adjusted); Sample 4, 10 mM Citric acid in 80% EtOH pH4; Sample 5, 10 mM Citrate in 80% EtOH pH5; Sample 6, 10 mM Citrate in 80% EtOH pH6; Sample 7, 10 mM Tris in 80% EtOH pH7; Sample 8, 10 mM Tricine in 80% EtOH pH8; Sample 9, 0.1% Ethanolamine in 80% EtOH pH9; Sample 10, 0.1% Ethanolamine in 80% EtOH pH10; Sample 11, 0.1% Ammonia in 80% EtOH pH<10 (not adjusted); Sample 12, 80% EtOH in H2O (pH not adjusted).

The results show that CBD recovery is not significantly affected by the pH of the selective solvent.

FIG. 13 shows optimized binding conditions for CBD using ion exchange chromatography (n=3). 0.1 g of hemp was heated to 120° C. and extracted 3× in 100% ethanol. Extracts of 0.5 g total hemp per replicate were pooled and diluted with $H_2O$ to the appropriate ethanol concentrations. Samples were loaded at 100% ethanol and decreasing to 10% ethanol onto the various resins (DEAE—FIG. 13A, CMS—FIG. 13B, HiQ—FIG. 13C, HiS—FIG. 13D. The Flow Throughs (FT) were collected and analyzed by LC-ESI-MS.

Figure 14A:
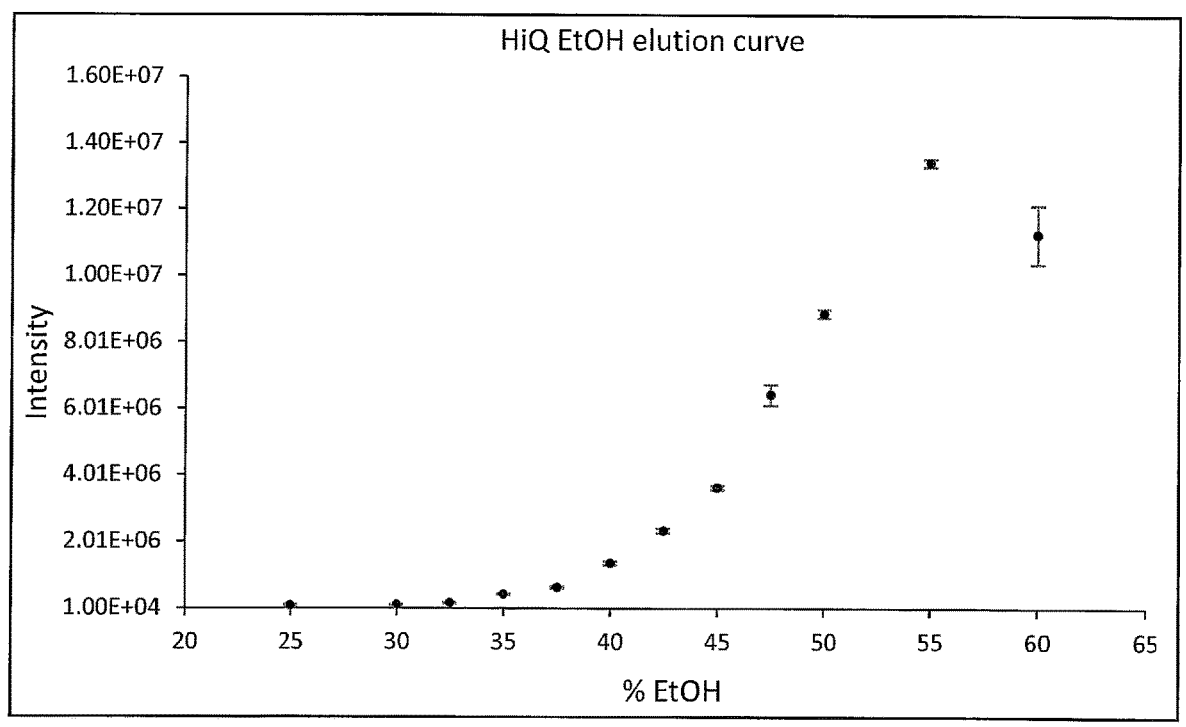
FIG. 14A. Elution curves in Ethanol for HiQ columns (n=3). ~7.5 mg CBD was extracted from 0.5 g hemp in 100% Ethanol, diluted to 20% ethanol and loaded onto a ~100 ul HiQ column. The column was washed with loading solvent prior to elution with increasing amounts of Ethanol (25, 30, 32.5, 35, 37.5, 40, 42.5, 45, 47.5, 50, 55 and 60%). Up to ~50%, the fractions are observed to be clear. Above 50%, the elutions become green. Fractions were collected and analyzed by LC-MS.
Figure 14B:
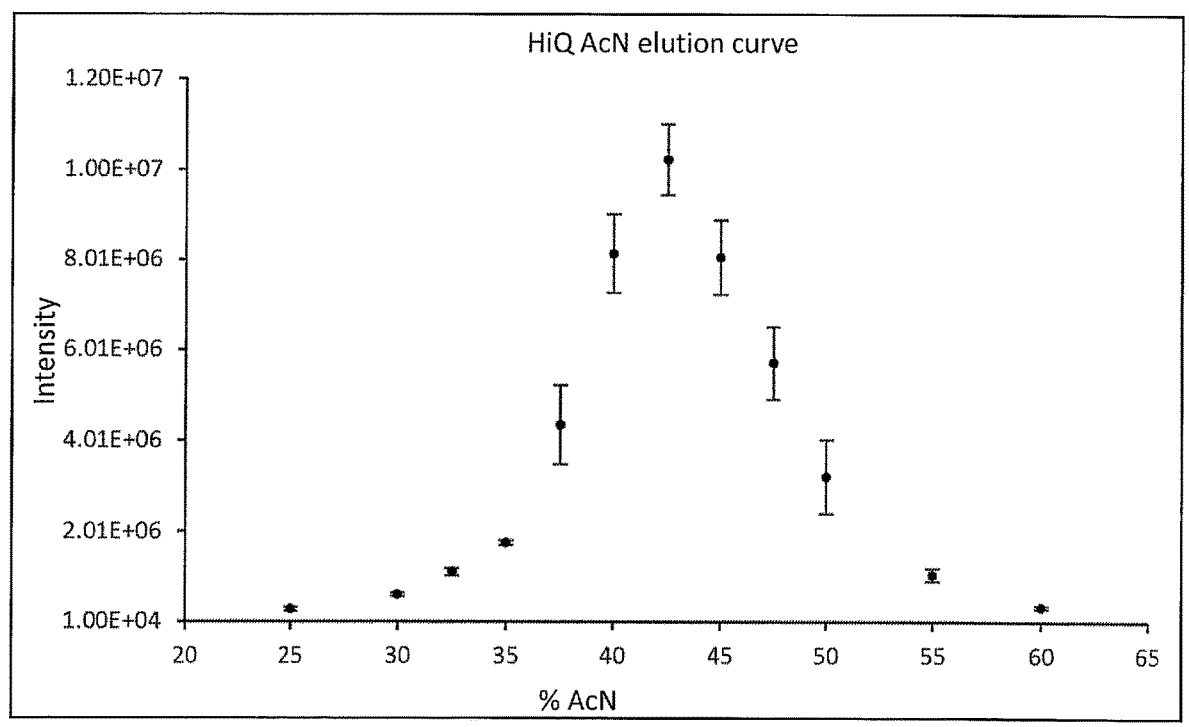
FIG. 14B. Elution curves in Acetonitrile for HiQ columns (n=3). ~7.5 mg CBD was extracted from 0.5 g hemp in 100% Acetonitrile, diluted to 20% acetonitrile and loaded onto a ~100 ul HiQ column. The column was washed with loading solvent prior to elution with increasing amounts of Acetonitrile (25, 30, 32.5, 35, 37.5, 40, 42.5, 45, 47.5, 50, 55 and 60%). Up to ~35%, the fractions are observed to be clear. Above 35%, the elutions become green (elutions separate in 2 distinct layers, one clear and one green). Fractions were collected and analyzed by LC-MS.

FIG. 14 shows elution curves in Ethanol or Acetonitrile for HiQ columns (n=3). FIG. 14A, ~7.5 mg CBD was extracted from 0.5 g hemp in 100% Ethanol, diluted to 20% ethanol and loaded onto a ~100 ul HiQ column. The column was washed with loading solvent prior to elution with increasing amounts of Ethanol (25, 30, 32.5, 35, 37.5, 40, 42.5, 45, 47.5, 50, 55 and 60%). Up to ~50%, the fractions are observed to be clear. Above 50%, the elutions become green. Fractions were collected and analyzed by LC-MS. FIG. 14B, ~7.5 mg CBD was extracted from 0.5 g hemp in 100% Acetonitrile, diluted to 20% acetonitrile and loaded onto a ~100 ul HiQ column. The column was washed with loading solvent prior to elution with increasing amounts of Acetonitrile (25, 30, 32.5, 35, 37.5, 40, 42.5, 45, 47.5, 50, 55 and 60%). Up to ~35%, the fractions are observed to be clear. Above 35%, the elutions become green (elutions separate in 2 distinct layers, one clear and one green). Fractions were collected and analyzed by LC-MS.

Figure 15:
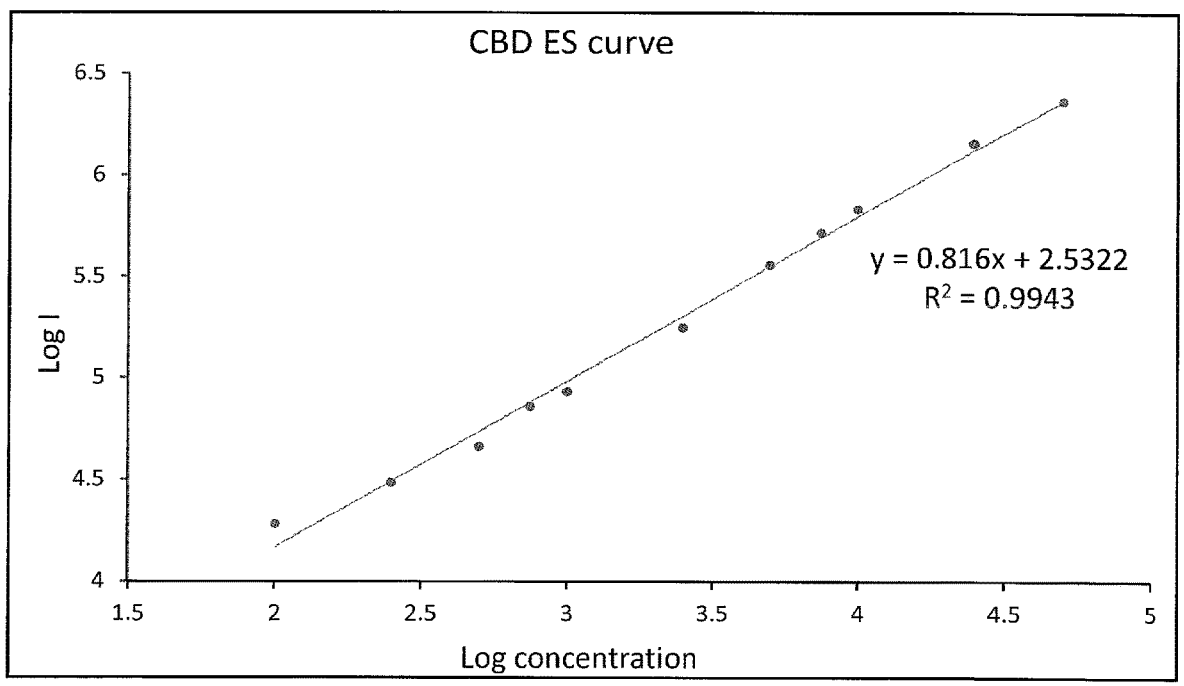
FIG. 15. CBD external standard curve 50-50,000 nM (n=2) measured by LC-ESI-MS/MS using isocratic separation over C18 resin.

FIG. 15 shows a CBD external standard curve 50-50,000 nM (n=2) measured by LC-ESI-MS/MS using isocratic separation over C18 resin.

Figure 16:
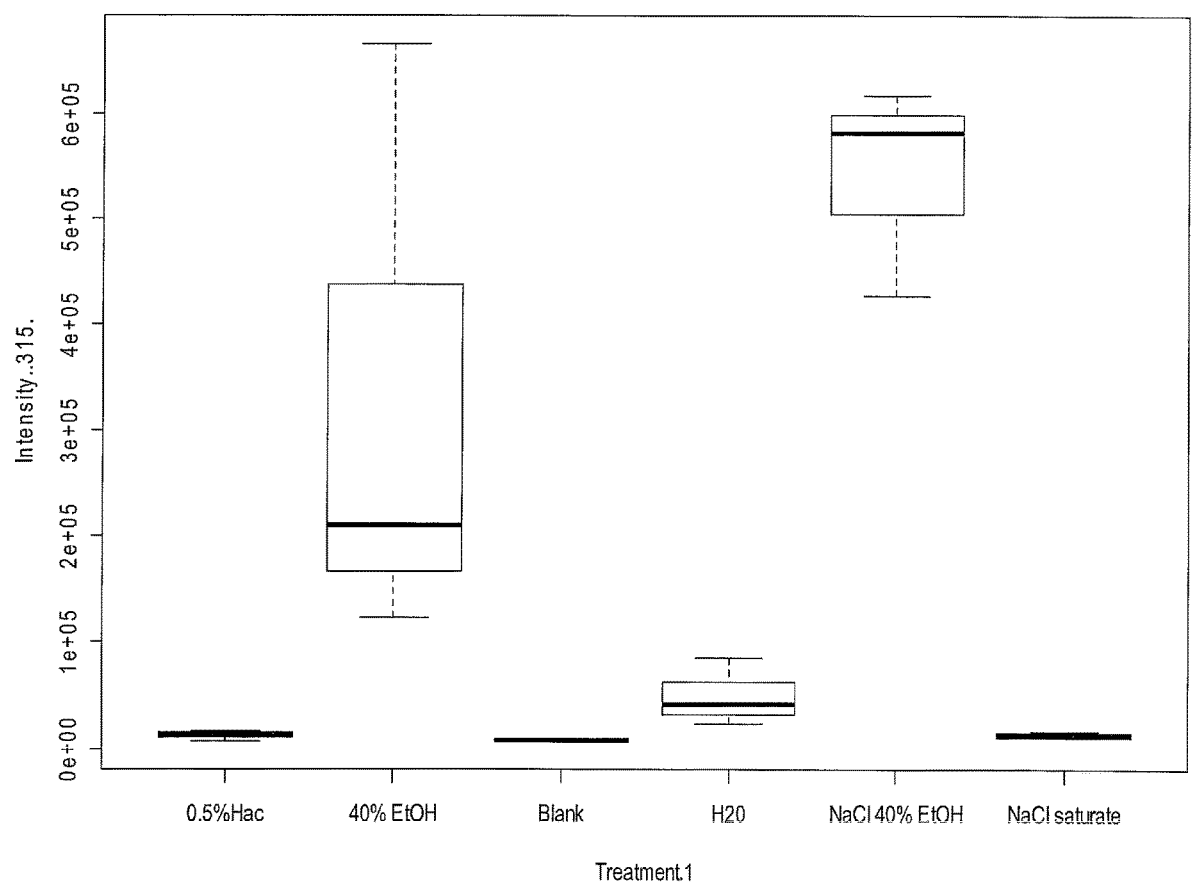
FIG. 16. The wash of intermediate resin from *cannabis* sample A. A 0.1 g aliquot of *cannabis* sample A was washed heated to 120° C. for 1 hour, extracted in ethanol and dried under vacuum to make a intermediate resin. The water soluble components of the resin were washed in water or water modified with organic acid, ethanol, or salt.

FIG. 16 shows the effect of a wash of intermediate resin from *cannabis* sample A. A 0.1 g aliquot of *cannabis* sample A was washed in water and heated to 120° C. for 1 hour, extracted in ethanol and dried under vacuum to make an intermediate resin. The water soluble components of the resin were washed in water or water modified with 0.5% acetic acid (v:v), 40% ethanol, salt/ethanol and saturated salt.

The results show that 40% ethanol was a better polar solvent in removing soluble compounds compared to the other solvents from the resin in sample A.

Figure 17:
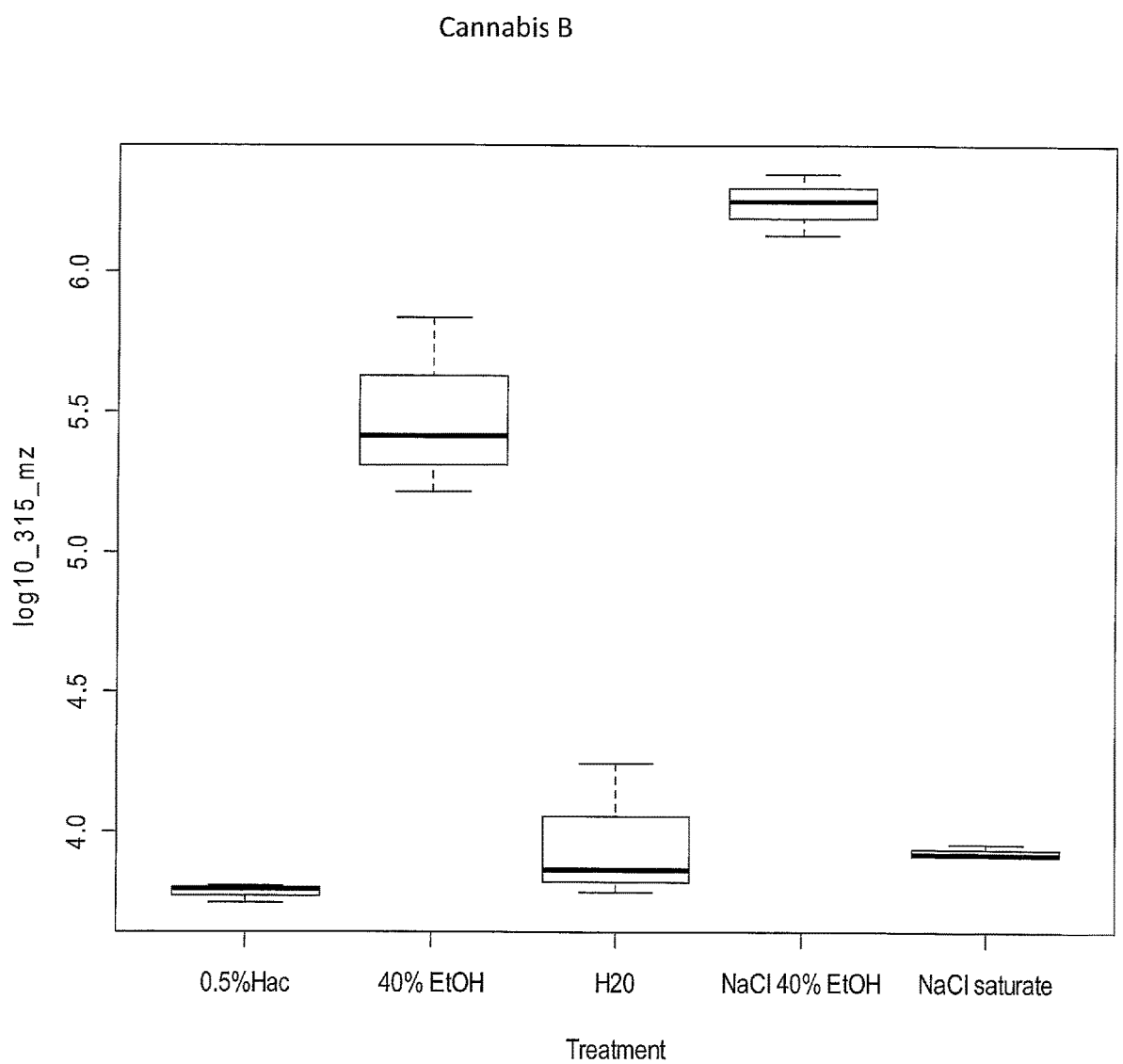
FIG. 17. The wash of intermediate resin from *cannabis* sample B. A 0.1 g aliquot of *cannabis* sample A was washed heated to 120° C. for 1 hour, extracted in ethanol and dried under vacuum to make an intermediate resin. The water soluble components of the resin were washed in water, water with 0.5% acetic acid (v:v), ethanol, or salt.

FIG. 17 shows the results of a wash of intermediate resin from *cannabis* sample B. A 0.1 g aliquot of *cannabis* sample A was washed in water and heated to 120° C. for 1 hour, extracted in ethanol and dried under vacuum to make an intermediate resin. The water soluble components of the resin were washed in water or water modified with 0.5% acetic acid, 40% ethanol, salt/ethanol and saturated salt. The results show that that 40% ethanol was a better polar solvent in removing soluble compounds compared to the other solvents from the resin in sample B.

Figure 18:
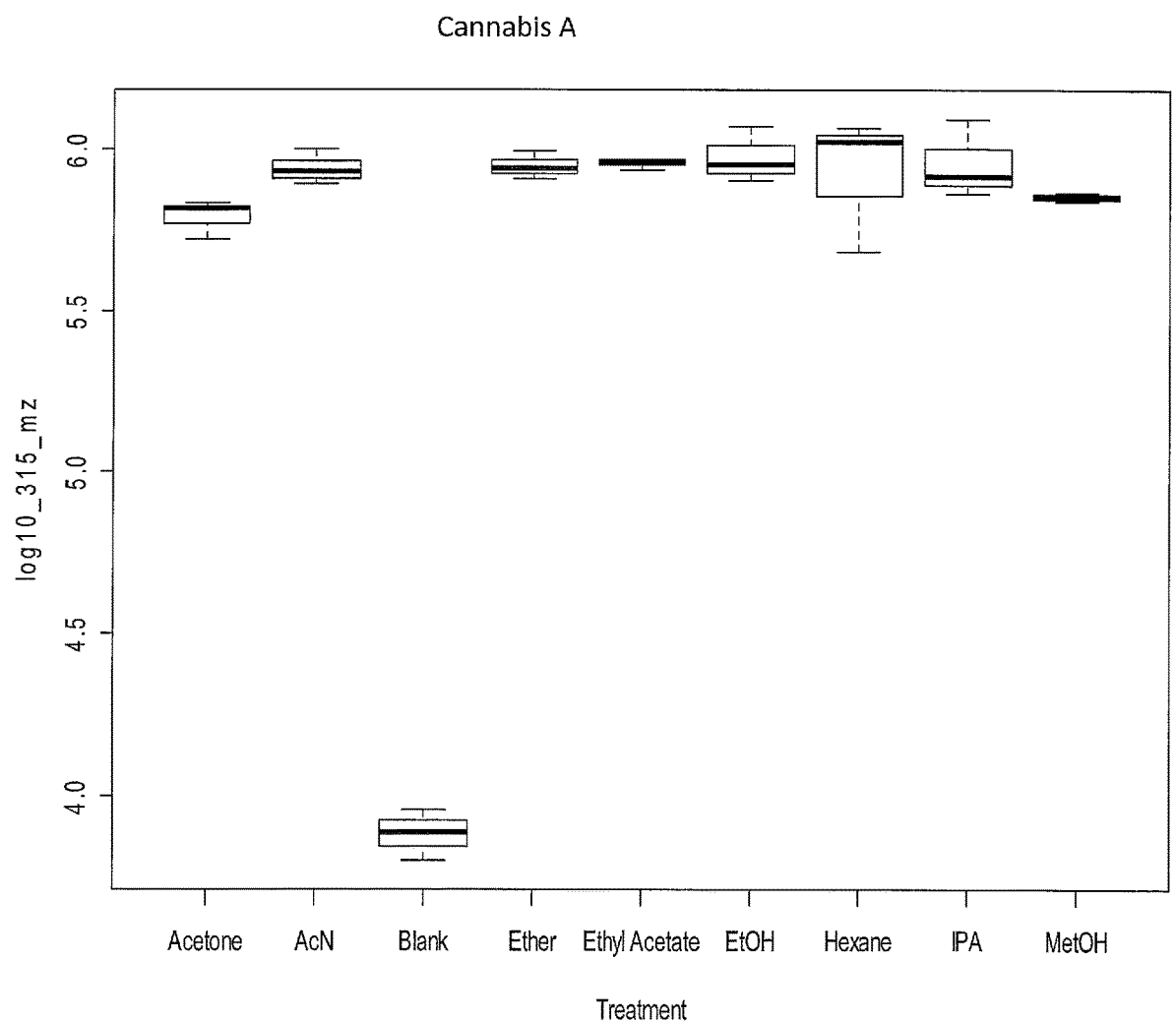
FIG. 18. The extraction of intermediate resin from *cannabis* sample A. A 0.1 g aliquot of *cannabis* sample A was washed heated to 120° C. for 1 hour, extracted in ethanol and dried under vacuum to make a intermediate resin. The water soluble components of the resin were washed in water with 0.5% acetic acid (v:v) and extracted with 1 ml of the solvent shown.

FIG. 18 shows the results of a selective extraction of intermediate resin from *cannabis* sample A. A 0.1 g aliquot of *cannabis* sample B was washed in water and heated to 120° C. for 1 hour, extracted in ethanol and dried under vacuum to make an intermediate resin. The water soluble components of the resin were washed in water modified with 0.5% acetic acid and extracted with 1 ml of the solvent shown.

Figure 19:
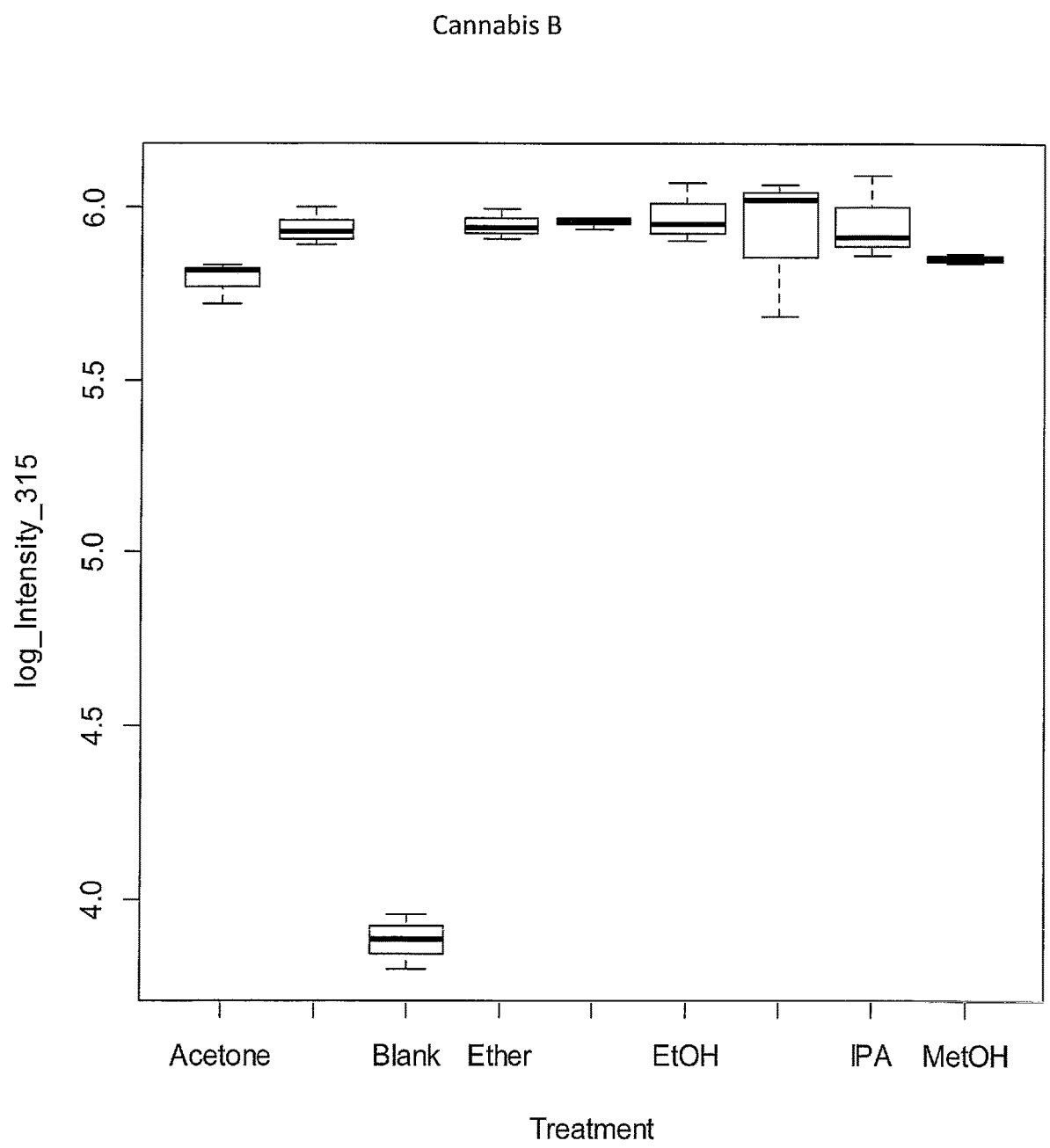
FIG. 19. The extraction of intermediate resin from *cannabis* sample B. A 0.1 g aliquot of *cannabis* sample B was washed heated to 120° C. for 1 hour, extracted in ethanol and dried under vacuum to make a intermediate resin. The water soluble components of the resin were washed in water with 0.5% acetic acid (v:v) and extracted with 1 ml of the solvent shown.

FIG. 19 shows the results of extraction of intermediate resin from *cannabis* sample B. A 0.1 g aliquot of *cannabis* sample B was washed in water and heated to 120° C. for 1 hour, extracted in ethanol and dried under vacuum to make a intermediate resin. The water soluble components of the resin were washed in water modified with 0.5% acetic acid and extracted with 1 ml of a solvent: acetone, acetonitrile, ether, ethyl acetate, ethanol, hexane, isopropyl alcohol, and methanol.

Definitions and Interpretation

The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. Embodiments were chosen and described in order to best explain the principles of the invention and the practical application, and to enable others of ordinary skill in the art to understand the invention for various embodiments with various modifications as are suited to the particular use contemplated. To the extent that the following description is of a specific embodiment or a particular use of the invention, it is intended to be illustrative only, and not limiting of the claimed invention.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to combine, affect or connect such aspect, feature, structure, or characteristic with other embodiments, whether or not such connection or combination is explicitly described. In other words, any element or feature may be combined with any other element or feature in different embodiments, unless there is an obvious or inherent incompatibility between the two, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all language such as "up to", "at least", "greater than", "less than", "more than", "or more", and the like, include the number recited, and such terms refer to ranges that can be subsequently broken down into sub-ranges as discussed above. In the same manner, all ratios recited herein also include all sub-ratios falling within the broader ratio.

The invention claimed is:

1. A method of extracting a cannabinoid from a *Cannabis* plant tissue comprising the steps:
   a) a heating step of heating the *Cannabis* plant tissue to convert carboxylated forms of the cannabinoid to a decarboxylated activated non-polar form of the cannabinoid in an activated *Cannabis* plant tissue;
   b) at least one washing step of washing the decarboxylated activated non-polar form of the cannabinoid or the activated *Cannabis* plant tissue with a polar solvent, wherein the polar solvent is polar and comprises water, wherein the polar solvent is removed as waste and thus selectively removes polar components that are soluble in the polar solvent, leaving the decarboxylated activated non-polar form of the cannabinoid; and
   c) an extraction step of selectively extracting the decarboxylated activated non-polar form of the cannabinoid using a potable selective solvent, wherein the potable selective solvent is an organic non-polar solvent, wherein the potable selective solvent comprises 80% ethanol in water, and wherein the extraction step is performed at a refrigerated temperature that is above a freezing temperature and below a flashpoint temperature of the potable selective solvent; and a vacuum drying step, after the extraction step, of drying the decarboxylated activated non-polar form of the cannabinoid under a vacuum at the refrigerated temperature to make an intermediate resin;
   wherein the extraction step is performed after the heating step; wherein the washing step is performed after the extraction step; and wherein, after the vacuum drying step, the intermediate resin is washed in the polar solvent.

2. The method of claim 1, wherein before the washing step, the *Cannabis* plant tissue is solid or has been processed to a powder or suspension.

3. The method of claim 1, wherein after the extraction step, the extracted cannabinoids is separated using chromatography including ion exchange or reverse phase.

4. The method of claim 3, wherein the separated cannabinoids is identified and/or quantified using mass spectrometry (MS).

5. The method of claim 1 wherein the polar solvent further comprises water modified by a salt, a non-ionic non-polymeric detergent or a bile salt, a sodium deoxycholate, a potable buffer, a potable phosphate or carbonate buffer, an organic acid, an acetic acid or formic acid, ammonia, ammonium hydroxide, methylamine trimethylamine, or ethanol, provided the ethanol is less than 40% (v:v).

6. The method of claim 5 wherein the polar solvent comprises less than 0.5% acetic acid in water by volume.

7. The method of claim 5 wherein the polar solvent comprises 40% ethanol in water by volume.

8. The method of claim 1 wherein the washing step is performed multiple times.

9. The method of claim 8 wherein the washing step is performed multiple times with a first polar solvent, followed by multiple washes with a second polar solvent, different from the first.

10. The method of claim 9 wherein the first polar solvent comprises water modified by an organic acid and the second polar solvent comprises ethanol.

11. The method of claim 8 wherein the washing step is performed at a temperature less than about 5° C.

12. The method of claim 1 wherein the refrigerated temperature is less than about 5° C.

13. The method of claim 12 wherein the refrigerated temperature is less than about 0° C.

14. The method of claim 5 wherein the polar solvent comprises less than 5.0% acetic acid in water by volume.

15. The method of claim 14 wherein the polar solvent comprises less than 1.0% acetic acid in water by volume.

16. The method of claim 10 wherein the first polar solvent comprises said water modified by an acetic acid.

17. The method of claim 10 wherein the second polar solvent comprises 40% ethanol in water.

* * * * *